United States Patent
Adachi et al.

(10) Patent No.: US 8,382,483 B2
(45) Date of Patent: Feb. 26, 2013

(54) SERVICE PROVIDING SYSTEM

(75) Inventors: Shinobu Adachi, Osaka (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 1098 days.

(21) Appl. No.: 12/295,396

(22) PCT Filed: Apr. 19, 2007

(86) PCT No.: PCT/JP2007/058544
§ 371 (c)(1),
(2), (4) Date: Sep. 30, 2008

(87) PCT Pub. No.: WO2007/148469
PCT Pub. Date: Dec. 27, 2007

(65) Prior Publication Data
US 2009/0142743 A1    Jun. 4, 2009

(30) Foreign Application Priority Data
Jun. 21, 2006    (JP) .................................. 2006-171863

(51) Int. Cl.
G09B 19/00    (2006.01)
G09B 3/00    (2006.01)
G09B 7/00    (2006.01)
A61B 5/04    (2006.01)
A61B 5/05    (2006.01)

(52) U.S. Cl. ........ 434/236; 434/322; 434/323; 600/407; 600/544; 600/545

(58) Field of Classification Search .................. 434/236, 434/322, 323; 600/407, 544, 545
See application file for complete search history.

(56) References Cited

U.S. PATENT DOCUMENTS 5,137,027 A * 8/1992 Rosenfeld ..................... 600/544
5,995,868 A * 11/1999 Dorfmeister et al. ......... 600/544
6,102,846 A * 8/2000 Patton et al. ..................... 600/26

(Continued)

FOREIGN PATENT DOCUMENTS

CN    1474306 A    2/2004
JP    10-078743    3/1998

(Continued)

OTHER PUBLICATIONS

Office Action for corresponding Chinese Application No. 200780009012.9 dated Apr. 27, 2010.

(Continued)

*Primary Examiner* — Nikolai A Gishnock
(74) *Attorney, Agent, or Firm* — Renner, Otto, Boisselle & Sklar, LLP

(57) ABSTRACT

There is provided a system which is able to realize study assistance or a desired appliance operation for a user, even in the absence of an answer input from the user.

A service providing system includes an output section for presenting a question to a user, and further presenting sequentially a plurality of options as candidate answers to the question; a signal detection section for measuring an event-related potential of electroencephalograms of the user; and a determination section for determining whether the user has thought each option to be the correct answer or not, based on the event-related potential in a predetermined period after each option is presented, e.g., in a period from about 350 milliseconds to about 450 milliseconds.

18 Claims, 23 Drawing Sheets

U.S. PATENT DOCUMENTS

| | | | |
|---|---|---|---|
| 6,309,342 B1 * | 10/2001 | Blazey et al. | 600/26 |
| 6,594,524 B2 * | 7/2003 | Esteller et al. | 607/45 |
| 2003/0013951 A1 * | 1/2003 | Stefanescu et al. | 600/407 |
| 2004/0068199 A1 * | 4/2004 | Echauz et al. | 600/544 |
| 2006/0101079 A1 * | 5/2006 | Morikawa et al. | 707/104.1 |

FOREIGN PATENT DOCUMENTS

| | | |
|---|---|---|
| JP | 2002-221893 | 8/2002 |
| JP | 1474306 A | 2/2004 |
| WO | 03/050782 | 6/2003 |
| WO | 2005/001677 A1 | 1/2005 |

OTHER PUBLICATIONS

International Search Report for corresponding Application No. PCT/JP2007/058544 dated May 22, 2007.

Akihiro Kojo et al.; "The Haar-Wavelet Transform of Event Related Brain Potentials"; Information Processing Society of Japan Kenkyu Hokoku; Sep. 14, 1995; vol. 95, No. 88; ISSN 0919-6072; pp. 1-8.

Shinichi Niwa et al.; "Event-Related Potential Event-Related Potential and Developments in Neuroinformation Society"; 1997; p. 189.

Shinichi NIWA et al.; "Event-Related Potential Event-Related Potential and Developments in Neuroinformation Society"; 1997; p. 189, and partial English translation thereof. (Previously identified in IDS filed on Sep. 30, 2008.

Tomas Hruby et al.; "Event-Related Potentials—the P3 Wave", Acta Neurobiol. Exp. 2003, 63, pp. 55-63.

Shinichi Niwa et al.; "Event-Related Potential Event-Related Potential and Developments in Neuroinformation *Science*". 1997; p. 189, and partial English translation thereof. (Previously identified in IDS filed on Sep. 30, 2008.

Tomas Hruby et al.; "Event-Related Potentials—the P3 Wave", Acta *Neurobial*. Exp. 2003, 63, pp. 55-63.

\* cited by examiner

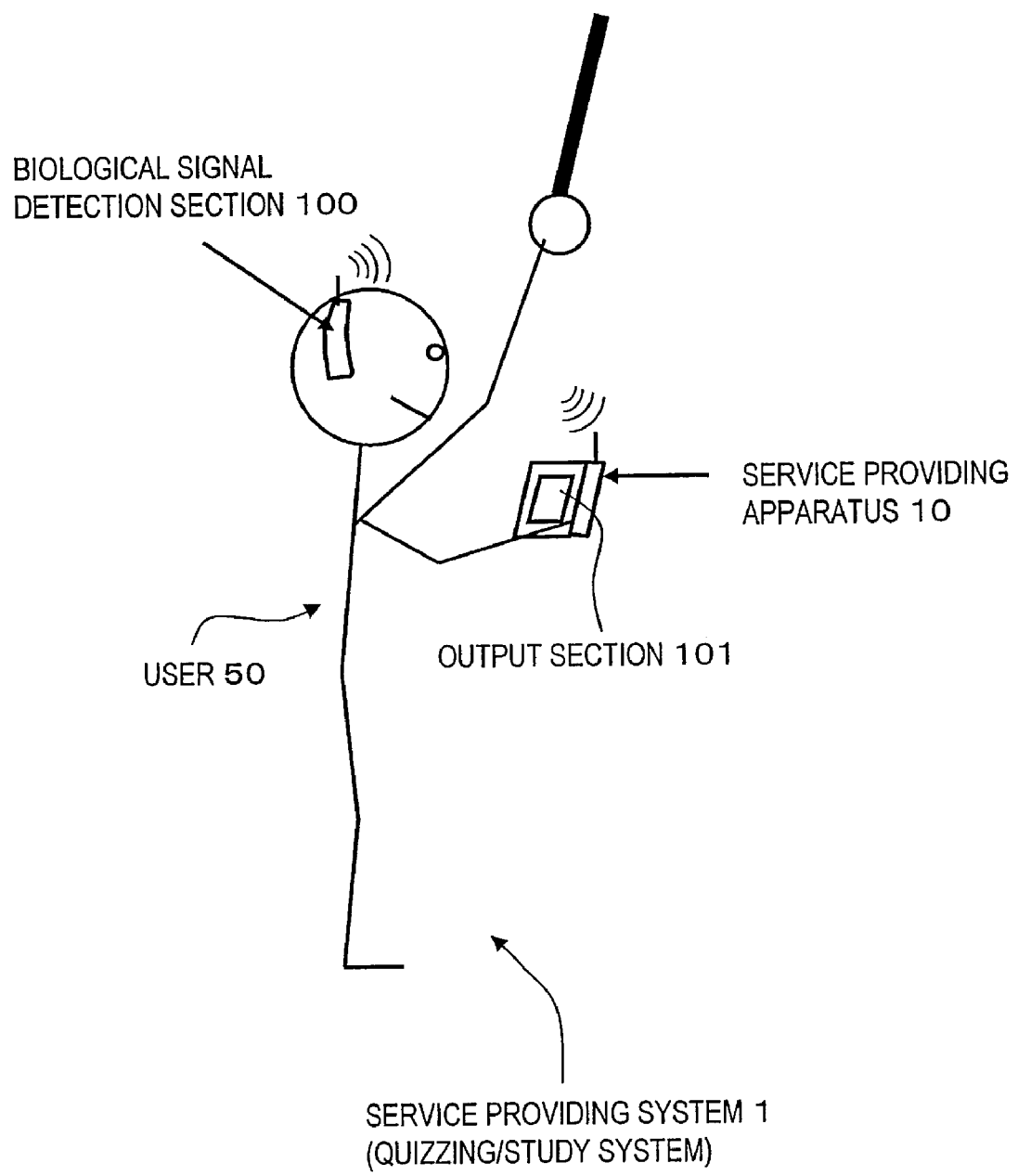

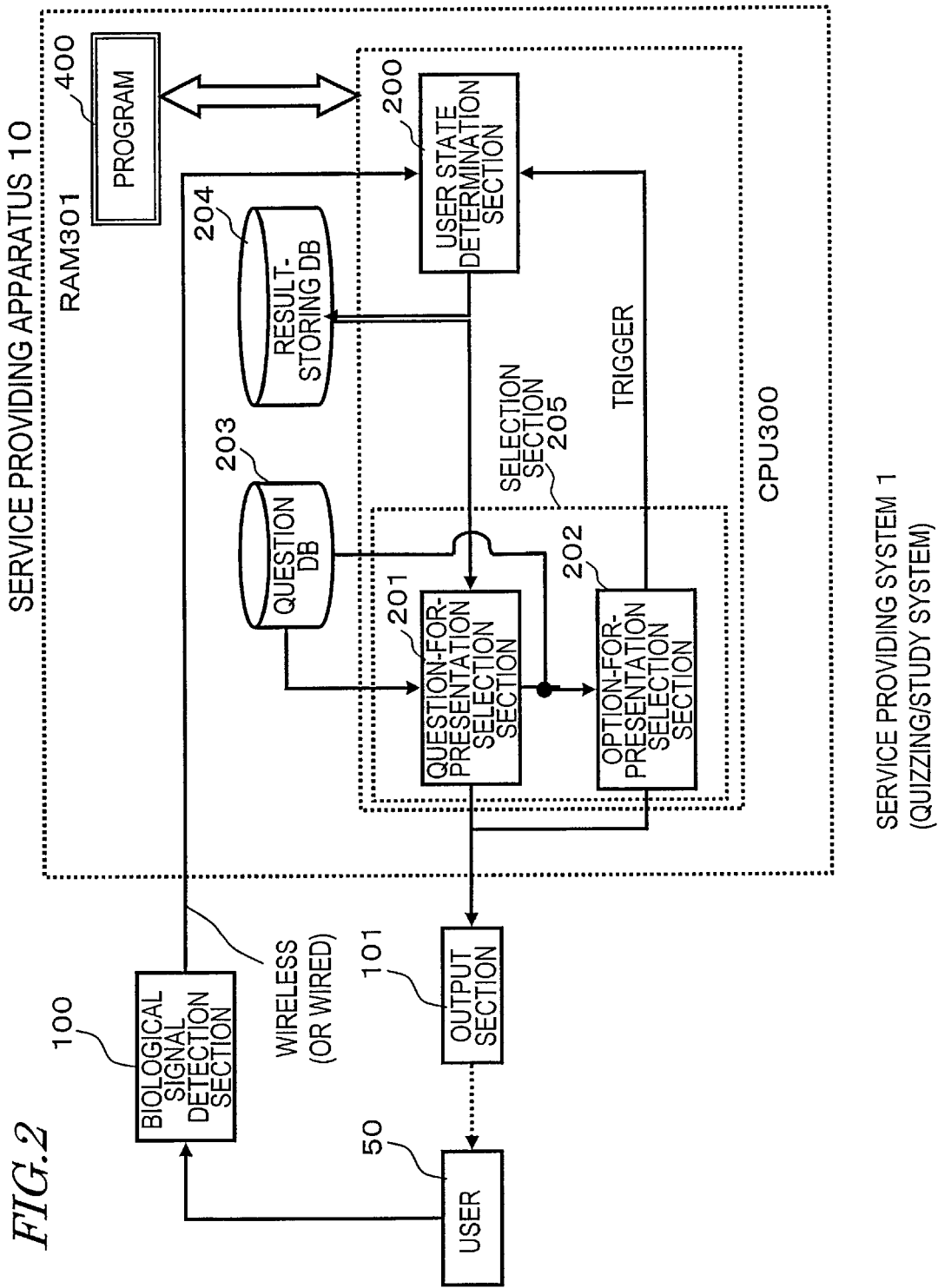

FIG.3

QUESTION DB 203

(a) SOCIETY

| | QUESTION | OPTION | | | | CORRECT ANSWER | IMPORTANCE LEVEL | GENRE |
|---|---|---|---|---|---|---|---|---|
| | | A | B | C | D | | | |
| 1 | WHO IS THE SHOGUN THAT ISSUED THE "SHORUI-AWAREMI-REI" ORDERS? | TSUNAYOSHI | IETSUNA | IEMITSU | IENOBU | A | 5 | HISTORY 7 |
| 2 | WHICH BOOK IS THE BASIS FOR THE WORDS OF THE NATIONAL ANTHEM "KIMIGAYO"? | MANYOSHU | KOJIKI | NIHONSHOKI | KOKINWAKASHU | D | 3 | HISTORY 11 |
| 3 | WHICH COUNTRY DOES NOT BELONG TO THE AFRICAN CONTINENT? | NIGERIA | KENYA | GUINEA | AUSTRIA | D | 1 | GEOGRAPHY 3 |
| 4 | WHICH PENINSULA HAS THE LARGEST AREA IN JAPAN? | SHIMOKITA PENINSULA | SHIRETOKO PENINSULA | ISE PENINSULA | BOSO PENINSULA | C | 4 | GEOGRAPHY 1 |
| 5 | WHO IS THE PHILOSOPHER THAT SAID "COGITO, ERGO SUM"? | PLATO | DESCARTES | KANT | SOCRATES | B | 3 | HISTORY 2 |
| | ⋮ | | | | | | | |

QUESTION DB 203

(b) ARITHMETIC

| | QUESTION | OPTION | | | | CORRECT ANSWER | IMPORTANCE LEVEL | GENRE |
|---|---|---|---|---|---|---|---|---|
| | | A | B | C | D | | | |
| 1 | 1+1= | 4 | 2 | 1 | 3 | B | 5 | ADDITION 1 |
| 2 | 3+6= | 9 | 4 | 7 | 2 | A | 5 | ADDITION 1 |
| 3 | 4+2= | 9 | 2 | 5 | 6 | D | 5 | ADDITION 1 |
| 4 | 7+4= | 8 | 11 | 15 | 10 | B | 5 | ADDITION 2 |
| 5 | 9+8= | 13 | 16 | 17 | 14 | C | 5 | ADDITION 2 |
| | ⋮ | | | | | | | |

FIG.4

REFERENCE TABLE FOR CALCULATING MAHALANOBIS DISTANCE 210

| TEST | AVERAGE POTENTIAL OF GROUP HAVING "THOUGHT IT TO BE THE CORRECT ANSWER" | AVERAGE POTENTIAL OF GROUP HAVING "NOT THOUGHT IT TO BE THE CORRECT ANSWER" |
|---|---|---|
| 1 | −1.4561 | −5.4347 |
| 2 | 0.2409 | −2.9504 |
| 3 | 6.3408 | −10.0242 |
| 4 | 5.7999 | 1.3596 |
| 5 | 7.7224 | −9.4022 |
| 6 | 5.8028 | 1.1017 |
| 7 | 0.2366 | 5.8596 |
| 8 | −1.7586 | 0.3271 |
| ... | ... | ... |

FIG.5

RESULT-STORING DB 204

| QUESTION NUMBER | OPTION A | OPTION B | OPTION C | OPTION D |
|---|---|---|---|---|
| 1 | 1 | 0 | 0 | 0 |
| 2 | 0 | 0 | 0 | 0 |
| 3 | 0 | 1 | 0 | 1 |
| 4 | 1 | 1 | 0 | 0 |
| 5 | 0 | −1 | 0 | 0 |
| ... | ... | ... | ... | ... |

1 : THOUGHT TO BE THE CORRECT ANSWER
0 : THOUGHT TO BE NOT THE CORRECT ANSWER
−1 : EXCLUDED DUE TO MIXING OF NOISE

FIG. 6

QUESTION-FOR-PRESENTATION SELECTION RULE TABLE 211

| | | CORRECT ANSWER OPTION IN QUESTION DB MATCHES THE "THOUGHT TO BE THE CORRECT ANSWER" OPTION IN RESULT-STORING DB? | |
|---|---|---|---|
| | | MATCHES | WRONG |
| NUMBER OF "THOUGHT TO BE THE CORRECT ANSWER" STORED IN RESULT-STORING DB | 0 | JUDGED AS NOT UNDERSTANDING, OR FAILING TO LOOK AT QUESTION, AND SIMILAR QUESTION IS ASKED | |
| | 1 | JUDGED AS UNDERSTANDING, QUESTION IN DIFFERENT GENRE IS ASKED | JUDGED AS MISTAKEN, AND QUESTION IN SAME GENRE IS ASKED |
| | 2 OR MORE | JUDGED AS NOT FULLY UNDERSTANDING, AND QUESTION IN SAME GENRE IS ASKED | JUDGED AS NOT UNDERSTANDING, AND QUESTION IN SAME GENRE IS ASKED |

FIG. 7

QUESTION-FOR-PRESENTATION SELECTION RULE TABLE 211

| QUESTION NUMBER | CORRECT ANSWER OPTION IN QUESTION DB 203 | DETERMINATION RESULT STORED IN RESULT-STORING DB 204 | | | | GENRE OF NEXT QUESTION |
|---|---|---|---|---|---|---|
| | | OPTION A | OPTION B | OPTION C | OPTION D | |
| 1 | A | 1 | 0 | 0 | 0 | DIFFERENT GENRE |
| 3 | D | 0 | 0 | 0 | 0 | SAME GENRE |
| 4 | D | 0 | 1 | 0 | 1 | SAME GENRE |
| 5 | C | 1 | 1 | 0 | 0 | SAME GENRE |
| 6 | B | 0 | -1 | 0 | 0 | SAME GENRE |
| ... | ... | ... | ... | ... | ... | |

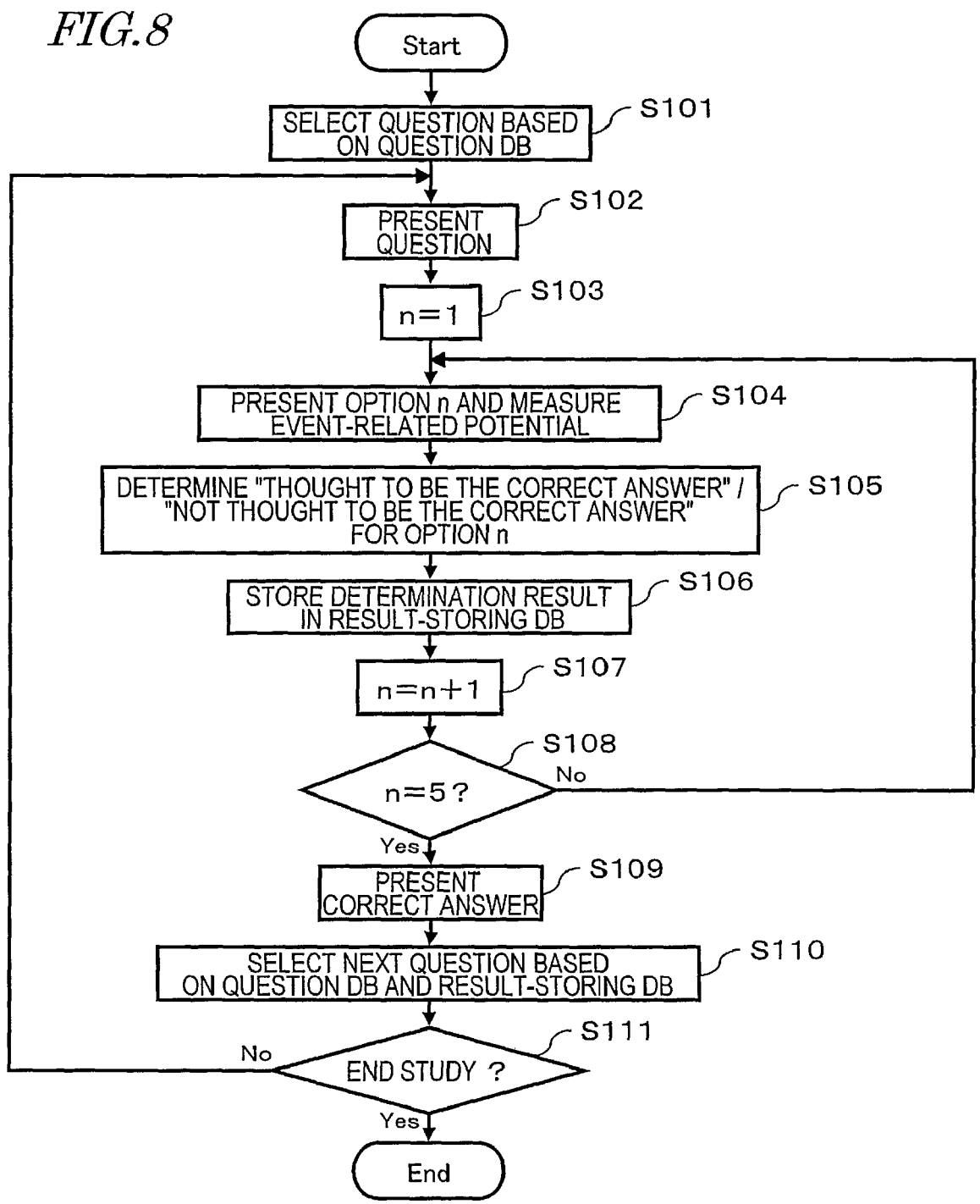

*FIG.16*

| | QUESTION | OPTION | | | | | | | | ORDER |
|---|---|---|---|---|---|---|---|---|---|---|
| | | A | | B | | C | | D | | |
| 1 | WHICH FUNCTION DO YOU WANT TO USE? | A | TV | B | VCR | C | MUSIC | D | GAME | 1 |
| 2 | WHICH TV PROGRAM DO YOU WANT TO WATCH? | A | PROGRAM NAME 1 | B | PROGRAM NAME 2 | C | PROGRAM NAME 3 | D | PROGRAM NAME 4 | 2 |
| 3 | "WHICH RECORDED PROGRAM DO YOU WANT TO WATCH? | A | PROGRAM NAME 11 | B | PROGRAM NAME 12 | C | PROGRAM NAME 13 | D | PROGRAM NAME 14 | 2 |
| 4 | WHICH MUSIC DO YOU WANT TO LISTEN? | A | MUSIC 1 | B | MUSIC 2 | C | MUSIC 3 | D | MUSIC 4 | 2 |
| 5 | WHICH GAME DO YOU WANT TO PLAY? | A | GAME 1 | B | GAME 2 | | | | | 2 |
| | ⋮ | | ⋮ | | ⋮ | | ⋮ | | | ⋮ |

SERVICE PROVIDING SYSTEM

TECHNICAL FIELD

The present invention relates to a technique of providing information or services for a user. More specifically, the present invention relates to an appliance and method for, even in the absence of an answer input from a user during study, distinguishing which option has been selected by the user by using as an index a biological signal such as electroencephalograms, and selecting and providing appropriate information or services for the user, and a computer program to be executed in such an appliance.

BACKGROUND ART

Study systems have conventionally been developed which present a question, receive an answer input from a user, and present information such as a correctness evaluation. Such study systems rely not only on an answer input by the user, but also on information related to the answer (e.g., the level or genre of the question to be next presented, as selected by the user), thus realizing an efficient study assistance.

For example, Patent Document 1 discloses a study system which measures the time required for answering, and presents a hint for any question that the user fails to answer within a predetermined time. In this study system, the question to be next presented is changed based not only on the scoring result of a test, but also on the frequency of presenting hints and the difficulty level of any question for which a hint has been presented.

Moreover, Patent Document 2 discloses a study system which, when a condition such as a question level is input, automatically selects an exercise. This study system collects degrees of confidence as a subjective evaluation by a user for each question, in the form of a questionnaire, during study. Then, based on the degree of confidence and the correctness result of the answer, the study system determines the degree of understanding of the user. Then, exercises are selected and asked in accordance with the inferred degree of understanding of the user.

Moreover, Patent Document 3 discloses a study system which utilizes a biological signal from a user. In order to maintain the user's will to study and enhance the efficiency of studying, this study system determines an arousal level or a stress level during study from a biological signal such as skin impedance or pulse waves, and realizes a selection of questions which, in conjunction with scoring results of a test, prevents the user's will to study from decreasing.

[Patent Document 1] Japanese Laid-Open Patent Publication No. 2002-221893

[Patent Document 2] Pamphlet of International Laid-Open No. 2003/050782

[Patent Document 3] Japanese Laid-Open Patent Publication No. 10-78743

DISCLOSURE OF INVENTION

Problems to be Solved by the Invention

In order to provide study assistance by using the study systems described in Patent Documents 1 to 3, an answer input from the user is indispensable. Therefore, such study systems are based on the premise that they are used in situations where the user is able to make an answer input (e.g., while being seated indoors). Thus, there is a problem in that study assistance of the study system does not function in a situation where both hands are full and it is difficult to make an answer input, e.g., on a train.

On the other hand, due to the prevalence of displays of sizes that allow casual transportation (mobile phones, game machines, PDAs, etc.) in the recent years, there is an increasing need of users to study anywhere and in any situation.

An objective of the present invention is to provide a system which is able to provide study assistance for a user even in the absence of an answer input from the user. More specifically, an objective of the present invention is to provide a system which is able to, even in the absence of an answer input from the user, determine which option is thought by the user to be a correct answer and provide study assistance in a manner similar to when there is an answer input, by using an event-related potential of a user during study.

Means for Solving the Problems

A service providing system according to the present invention comprises: an output section for presenting a question to a user, and further presenting sequentially a plurality of options as candidate answers to the question; a signal detection section for measuring an event-related potential of electroencephalograms of the user; and a determination section for determining whether the user has thought each option to be a correct answer or not, based on the event-related potential in a predetermined period after each option is presented.

The determination section may determine whether the user has thought each option to be a correct answer or not, by using as the predetermined period a period from about 350 milliseconds to about 450 milliseconds as counted from a point in time where each option is presented.

The service providing system may further comprise: a result-storing database for storing determination results in association with the question; and a selection section for selecting a question to be presented to the user from among a plurality of questions, based on the determination results.

The service providing system may further comprise a database storing the plurality of questions and a plurality of options which are candidate answers to each question, wherein, referring to the database, the selection section may select a question to be presented to the user and the plurality of options.

The service providing system may further comprise: a database storing a predetermined question as well as an option which is a correct answer to the predetermined question and an option which is not the correct answer; and a selection section for selecting the question by referring to the database, and thereafter selecting the option which is the correct answer or the option which is not the correct answer in an arbitrary order and sending the option to the output section, wherein, when beginning boot of the service providing system or when receiving an instruction from the user, based on an event-related potential after presenting the option which is the correct answer and an event-related potential after presenting the option which is not the correct answer, the determination section may execute a calibration for the event-related potential related to the user having thought it to be the correct answer.

The service providing system may further comprise a timing control section for determining whether the user is in a stand-by state or not based on the event-related potential in a predetermined period before presenting each option, and giving an instruction to select and output a next option in accordance with a determination result.

When the determination section determines that the user has thought the presented option to be the correct answer, the output section may not present any option that is left as a candidate answer to the question.

In the database, at least one of the plurality of options may represent the correct answer to the question; when determining that the user has thought the presented option to be the correct answer, the determination section may further determine whether the presented option matches the option which is the correct answer or not; and if they match, the output section may not present any option that is left as a candidate answer to the question.

When determining that the user has thought the presented option to be the correct answer, the determination section may present the option which is the correct answer.

When detecting that noise is mixed in the event-related potential based on the event-related potential, the determination section may quit the determination as to whether the user has thought the presented option to be the correct answer; and the output section may again present the option.

The selection section may present an option which is the correct answer at an $(n/2)^{th}$ or earlier, where n is a number of the plurality of options.

The determination section may previously retain, regarding a predetermined question, a threshold which lies between an average potential of an event-related potential in a time slot from 300 milliseconds to 500 milliseconds after presenting an option which is determined as having been thought to be the correct answer by the user and an average potential of an event-related potential in the time slot, which is determined as having not thought to be the correct answer; and the determination section may compare between the threshold and the average potential of the event-related potential in the time slot, and determine that the user has thought it to be the correct answer if the average potential is greater than the threshold, and determine that the user has not thought it to be the correct answer if the average potential is smaller than the threshold.

The determination section may retain, regarding a predetermined question, first numerical values which are pre-generated based on an average potential of an event-related potential in a time slot from 300 milliseconds to 500 milliseconds after presenting an option which is determined as having been thought to be the correct answer by the user and second numerical values which are pre-generated based on an average potential of an event-related potential in the time slot, which is determined as having not thought to be the correct answer; and the determination section may compare a first Mahalanobis distance between the average potential of the event-related potential in the time slot and the first numerical values against a second Mahalanobis distance between the average potential and the second numerical values, and determine that the user has thought it to be the correct answer if the first Mahalanobis distance is shorter than the second Mahalanobis distance, and determine that the user has not thought it to be the correct answer if the first Mahalanobis distance is longer than the second Mahalanobis distance.

The determination section may retain, regarding a predetermined question, a first template which is pre-generated based on an event-related potential in a time slot from 300 milliseconds to 500 milliseconds after presenting an option which is determined as having been thought to be the correct answer by the user and a second template which is pre-generated based on an event-related potential in the time slot, which is determined as having not thought to be the correct answer; and the determination section may compare a first correlation coefficient between a waveform value of the event-related potential in the time slot and the first template against a second correlation coefficient between the waveform value and the second template, and determine that the user has thought it to be the correct answer if the first correlation coefficient is greater than the second correlation coefficient, and determine that the user has not thought it to be the correct answer if the first correlation coefficient is smaller than the second correlation coefficient.

The determination section may retain an average value of the event-related potential corresponding to each of the plurality of options, and determine that an option having a largest average value has been thought to be the correct answer by the user.

Among the event-related potentials corresponding respectively to the plurality of options, the determination section may determine that an option having a shortest Mahalanobis distance from the first numerical values has been thought to be the correct answer by the user.

Among the event-related potentials corresponding respectively to the plurality of options, the determination section may determine that an option having a largest first correlation coefficient has been thought to be the correct answer by the user.

A quizzing method according to the present invention comprises the steps of: presenting a question to a user; sequentially presenting a plurality of options as candidate answers to the question; measuring an event-related potential of electroencephalograms of the user; and determining whether the user has thought each option to be a correct answer or not, based on the event-related potential in a predetermined period after each option is presented.

A computer program according to the present invention is executable on a computer, and the computer program causes the computer to execute the steps of: presenting a question to a user via an output device; sequentially presenting a plurality of options as candidate answers to the question; measuring an event-related potential of electroencephalograms of the user; and determining whether the user has thought each option to be a correct answer or not based on the event-related potential in a predetermined period after each option is presented.

Effects of the Invention

According to the present invention, after a question is presented, a plurality of options are sequentially presented as candidate answers to the question.

Based on an event-related potential in a predetermined period as counted from the point in time at which each option is presented (e.g., from about 350 milliseconds to about 450 milliseconds), it is determined whether the user has thought each option to be the correct answer or not. Since it is determined whether the user has thought each option to be the correct answer or not based on whether a positive component appears in the event-related potential during that period, there is no need for the user to input an answer. Therefore, in a situation where it is difficult to make an answer input, as in studying on a train, or in studying where no answer inputs are made, a study system which is capable of providing study assistance in a manner similar to when there is an answer input is realized, whereby the situations where the study system can be used and the methods of use are remarkably expanded.

BRIEF DESCRIPTION OF DRAWINGS

FIG. 1 A diagram showing an exemplary construction of a service providing system 1 according to Embodiment 1.

FIG. 2 A diagram showing the functional block construction of the service providing system 1 according to the present embodiment.

FIGS. 3 (a) and (b) are diagrams showing specific examples of data concerning questions stored in a question DB 203.

FIG. 4 A diagram showing an example of a reference table 210 for calculating Mahalanobis distances.

FIG. 5 A diagram showing an exemplary data structure of a result-storing DB 204.

FIG. 6 A diagram showing an exemplary data structure of a question-for-presentation selection rule table 211.

FIG. 7 A diagram showing another exemplary data structure of the question-for-presentation selection rule table 211.

FIG. 8 A flowchart showing a procedure of processing by the service providing system 1.

FIG. 16 A diagram showing a specific example of data concerning questions stored in an appliance manipulation DB 703.

DESCRIPTION OF THE REFERENCE NUMERALS

| | |
|---|---|
| 1-4 | service providing system |
| 10-13 | service providing apparatus |
| 100 | biological signal detection section |
| 101 | output section |
| 200, 600, 700 | user state determination section |
| 201 | question-for-presentation selection section |
| 202, 302, 601 | option-for-presentation selection section |
| 203 | question DB |
| 204 | result-storing DB |
| 205-208 | selection section |
| 300 | CPU |
| 301 | RAM |
| 400 | program |
| 500 | presentation timing control section |
| 701 | question-for-presentation selection section |
| 702 | option-for-presentation selection section |
| 703 | appliance operation DB |
| 800 | appliance operation control section |

BEST MODE FOR CARRYING OUT THE INVENTION

Hereinafter, with reference to the attached drawings, embodiments of the service providing system and apparatus according to the present invention will be described.

The inventors have found that, when options of a multiple-choice question are consecutively presented one by one, a characteristic feature appears in the event-related potential point at about 400 ms (milliseconds) since the option presentation as a starting point, in connection with whether the user has thought that option to be the correct answer or not. It has also been found that, without an answer input from the user, it is possible to determine an option that the user has thought to be the correct answer, by relying on the characteristic feature appearing in the event-related potential.

The "event-related potential" (ERP) is a portion of the electroencephalograms, referring to a transient potential fluctuation in the brain which occurs in temporal relationship with an external or internal event, respectively referred to as an extrinsic component or an intrinsic component. It is said that an external component is an evoked potential (which is passive and extrinsic) that relies on an external sensory stimulation, and that an intrinsic component is an intrinsic potential which fluctuates so as to reflect the cognitive attitude (degree of motivation toward a task) of the test subject with respect to an external stimulation (event).

Hereinafter, with reference to FIG. 18 to FIG. 25, an event-related potential measuring experiment that was performed by the inventors will be described first, in order to show the fact that whether a user has thought each option presented one by one to be the correct answer or not will appear in the event-related potential at about 400 milliseconds since the point of option presentation as a starting point. Thereafter, with reference to FIG. 1 to FIG. 17, embodiments of the present invention will be described.

1. Event-Related Potential Measuring Experiment

Figure 18:
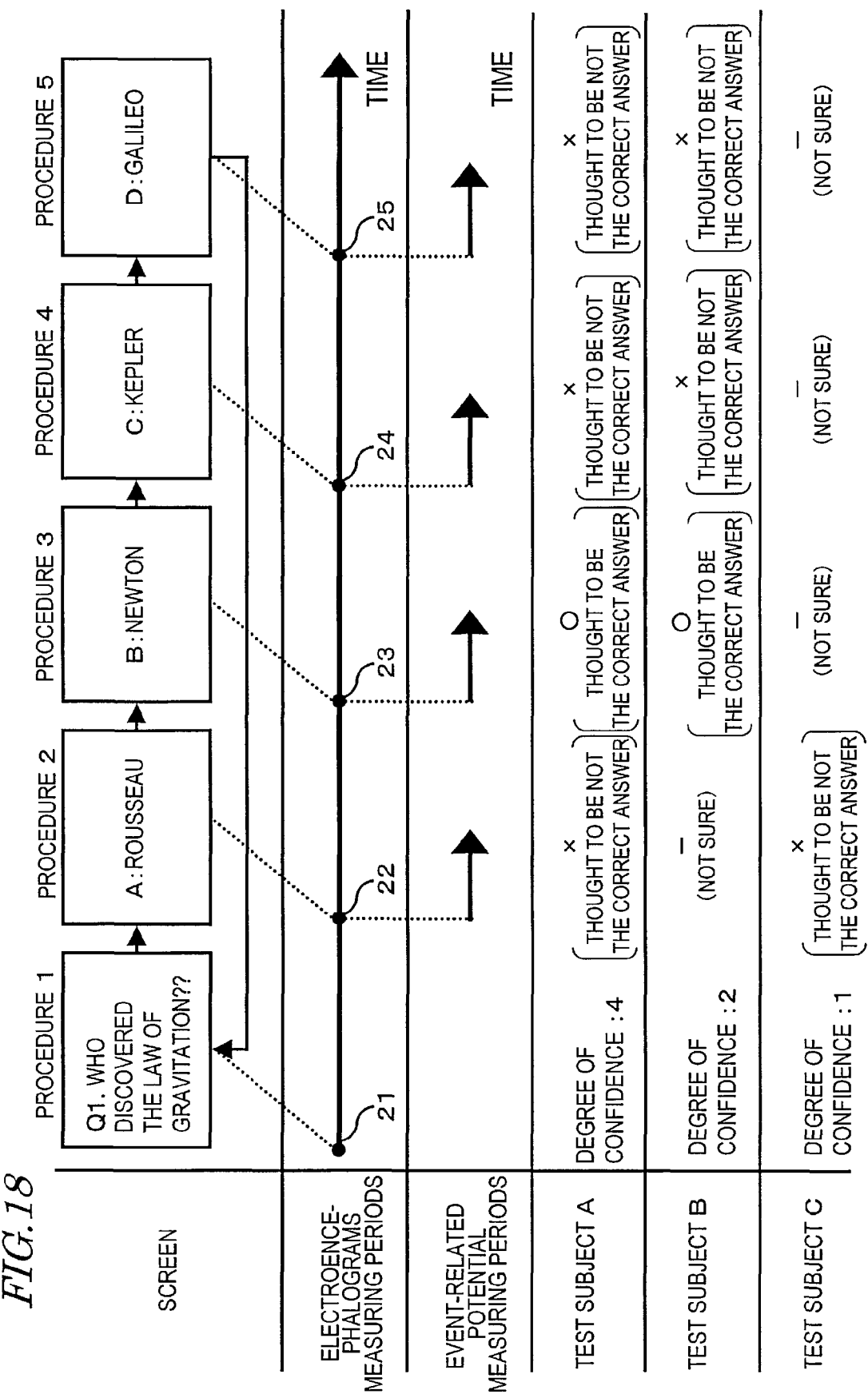
FIG. 18 A diagram showing the outline of an experimental procedure.

FIG. 18 is a diagram showing the outline of the experimental procedure. This experiment consists of the following steps: only a question is first presented to a test subject (step 1); thereafter, answer options for the question are consecutively presented (step 2 to step 5). As indicated by electroencephalograms measuring periods in FIG. 18, the electroencephalograms are always being measured during the experiment.

The following instructions were given to the test subject before the experiment. "First, only the question will be presented. Think of an answer to that question, and then write down your degree of confidence for that question on a separate piece of paper, 4 for confident and 1 for unconfident. After writing down the degree of confidence, move your gaze to the fixation point, and press the space key. Option A will be presented in 1 second after the key is pressed. Look well (for 1 second or more) at option A, and write down your evaluation as to whether you thought option A to be the correct answer or not on the separate piece of paper. Thought it to be the correct answer: ◯; Thought it to be not the correct answer: X; Not sure: —. After writing it down, move your gaze to the fixation point on the screen, and press the space key. In 1 second after the key is pressed, option B will be presented. And so on so forth, regarding options B, C, and D, similarly make evaluations as to whether you thought them to be the correct answer or not, and press the space key. There are 40 questions in total". Note that the pressing of the space key, which the test subject is instructed to do, is an input made to determine the timing for presenting the next question or option, and not an answer input. Moreover, the evaluations (◯, X, —) concerning the options are not necessary in practice, but are intended for the purpose of experimentally determining the subjective evaluations and event-related potential of the test subject.

The event-related potential measuring periods illustrated in FIG. 18 schematically indicate that, out of the electroencephalograms which are always being measured, the event-related potential is to be measured by using the point where the answer option is presented (point 22 to point 25 in FIG. 18) as a starting point.

FIG. 18 also shows examples of degrees of confidence concerning a question and evaluations of the options that test subjects have written down on a separate piece of paper. In FIG. 18, test subject A has a high degree of confidence and the option which he or she thought to be the correct answer is the correct answer, and therefore it is presumable that test subject A clearly knew the correct answer by just looking at the question. Test subject B has a low degree of confidence but the option which he or she thought to be the correct answer is the correct answer, and therefore it is presumable that test subject B did not know by just looking at the question but, among the options, found an option which he or she thought to be the correct answer. Test subject C has a low degree of confidence and no option exists that he or she thought to be the correct answer, and therefore it is presumable that test subject C did not know either by looking at the question or the options.

Figure 19:
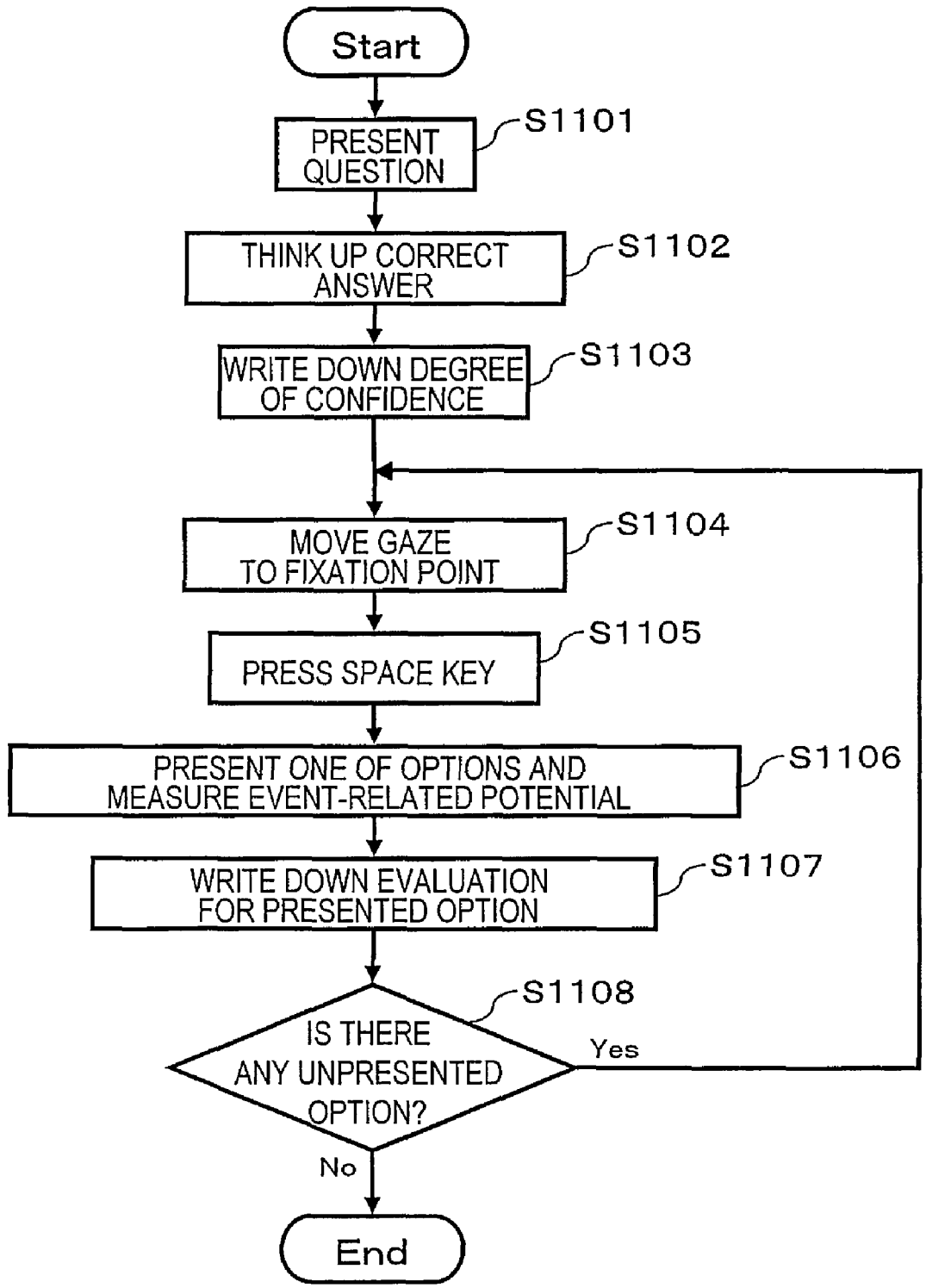
FIG. 19 A flowchart showing an experimental procedure corresponding to one question.

Next, the specific experimental procedure will be described. FIG. 19 shows an experimental procedure corresponding to one question. The experiment employed a 4-choice question, from option A to option D. First, at a point 21, the appliance presents only the question on the screen (S1101). The test subject thinks of a correct answer for that question (S1102); writes down on a separate piece of paper his or her degree of confidence for correctly answering that question, in four levels (S1103); moves his or her gaze to a fixation point (S1104); and presses the space key (S1105). The appliance presents one of the options (option A) at a point 22 (1 second after the key is pressed), and at the same time, measures the event-related potential by using the timing of presentation as a starting point (S1106). Note that each option to be presented had a content that was immediately recognizable to the test subject. By looking at the presented option, the test subject writes downs on the separate piece of paper an evaluation as to whether he or she thought it to be the correct answer or not (S1107). If there is any option that is yet to be presented, control proceeds to step S1104; if there is not, control proceeds to End (S1108); thereafter, step S1104 to step S1108 are repeated to present option B, option C, and option D.

Figure 20:
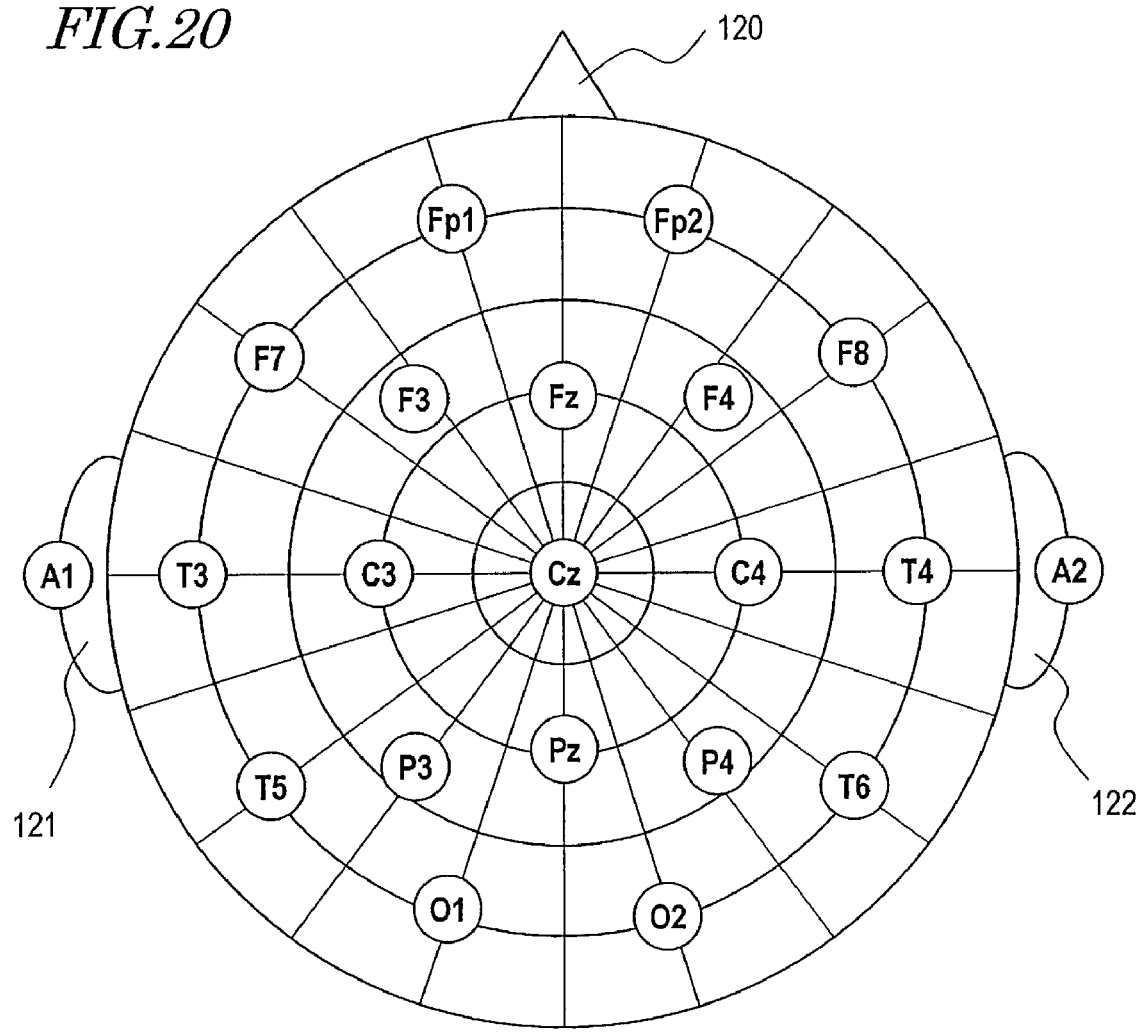
FIG. 20 A diagram showing positions at which electrodes for measuring electroencephalograms of a test subject are attached.

FIG. 20 shows positions at which electrodes for measuring the electroencephalograms of a test subject are attached. These attachment positions comply with the International 10-20 system. As an aid for clarifying the positional relationship, a nose 120, a left ear 121, and a right ear 122 of the test subject are shown in FIG. 20. In FIG. 20, any electrode that is on a median line which is equidistant from the left ear 121 and the right ear 122 and passes through the nose 120 is labeled as "z".

The electrodes for measuring the event-related potential were attached at 1) Fz: median forehead, 2) Cz: median center, 3) Pz: median vertex, 4) EOG: above the right eye, 5) 6) A1,A2: both earlobes, 7) body ground, and (Z): root of nose. The sampling frequency was 200 Hz, and the time constant was 3 seconds.

In the analysis of the experimental data, a 0.05 to 20 Hz band-pass filter was used, and the data from a period of 200 milliseconds before the option presentation was used for baseline correction. Moreover, in all channels, any channel resulting in an amplitude of 100 μV or more was excluded from the arithmetic mean for fear of noises (e.g. electrooculoar) being mixed.

Figure 21:
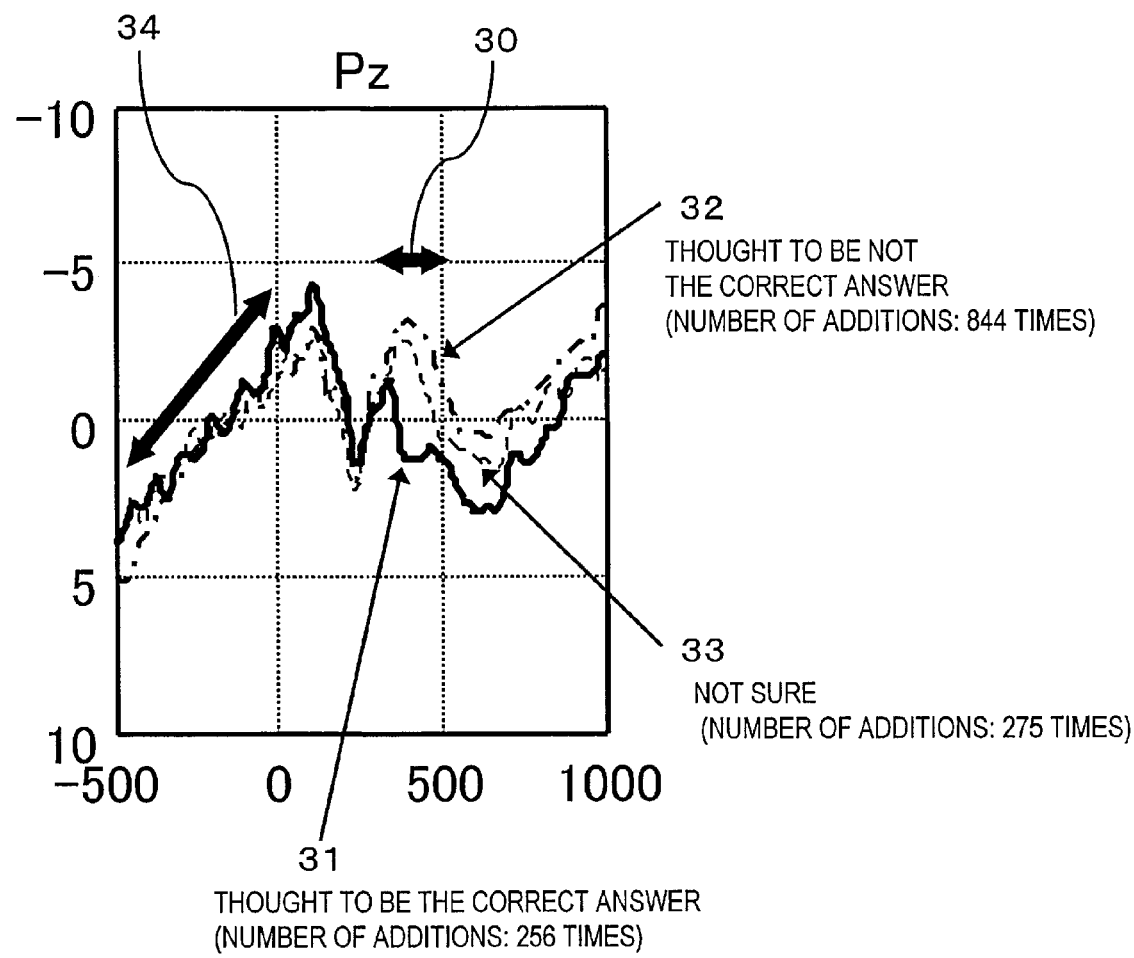
FIG. 21 A diagram showing waveforms of event-related potentials which were obtained as experimental results.

FIG. 21 shows waveforms of event-related potentials which were obtained as experimental results. These waveforms were obtained by taking total arithmetic means of experimental data of eleven test subjects, where the starting point is the point of option presentation. The horizontal axis of the graph represents time (in units of milliseconds), and the point of option presentation is at 0 millisecond. The vertical axis of the graph represents potential in units of μV. Note that the vertical axis is indicated so as to read minus in the upper direction and plus in the lower direction.

FIG. 21 shows three waveforms 31, 32, and 33. The three waveforms were obtained by individually taking a total arithmetic mean of the event-related potential measured at the position Pz shown in FIG. 19, based on the evaluations concerning options which were written down by the test subjects during the experiment (Thought it to be the correct answer: ◯; Thought it to be not the correct answer: X; Not sure: —).

The waveform 31 (solid line) shows a total arithmetic mean waveform of when presenting options which the test subjects evaluated as being "thought to be the correct answers", where the number of additions was 256 times.

The waveform 32 (dot-dash line) shows a total arithmetic mean waveform of when presenting options which the test subjects evaluated as being "thought to be not the correct answers", where the number of additions was 844 times.

The waveform 33 (dotted line) shows a total arithmetic mean waveform of when presenting options which the test subjects evaluated as being "not sure", where the number of additions was 275 times.

Now, attention should be paid to the waveform in a period 30 after the lapse of about 400 milliseconds since the point of option presentation (0 millisecond). Note that, in the present specification, the period 30 is supposed to be a periods from about 350 milliseconds to about 450 milliseconds as counted from 0 millisecond.

In the period 30, the waveform 31 corresponding to the evaluation of "thought to be the correct answer" is shifted in the positive direction, that is, a positive component is present. On the other hand, the other waveforms 32 and 33 are shifted in the negative direction, that is, a negative component is present.

Thus it is understood that, in the period 30, the waveform 31 and the waveforms 32 and 33 have clearly different characteristic features. Usually the event-related potential requires an arithmetic mean over about 20 times in order to reduce the influences of background electroencephalograms. However, since a large number of additions are made for each of the waveform 31 to waveform 33, it is unlikely that this difference in waveforms is a noise. These results and discussions together indicate that, by using an event-related potential at about 400 milliseconds since the option presentation, it is possible to determine whether a user has thought an option to be the correct answer or not.

As is clarified by this experiment, for each option of a multiple-choice question that is consecutively presented, depending on whether or not the test subject has thought it to be the correct answer or not, a clear difference appears at about 400 milliseconds since the point of option presentation in the event-related potential which is measured by an electroencephalograph. Therefore, by using this difference in the event-related potential, without an answer input, it is possible to determine whether the user has thought each consecutively presented option to be the correct answer or not.

Note that a zone 34 shown in FIG. 21 represents a zone in which a waveform component, called the CNV component, is present. The CNV component will be described later.

2. Distinction of Event-Related Potential Waveform

Now, a method of determining whether a user has thought an option to be the correct answer or not will be described. Since the amplitude of an event-related potential is as small as 1/10 of that of the background electroencephalograms, it is said to be difficult to distinguish with a simple technique of applying threshold processing to the peak values of the potential waveform. On the other hand, as shown in FIG. 21, the difference which appears in the event-related potential in connection with having thought to be the correct answer or not is observed as a potential difference and the shape of a waveform at about 400 milliseconds since the point of option presentation (thought to be the correct answer: projecting downwards; otherwise: projecting upwards). Therefore, determination is made by using as an index an average potential or correlation coefficient at about 400 milliseconds since the point of option presentation. Hereinafter, with reference to FIG. 22 to FIG. 25, methods for determining an option which the user has thought to be the correct answer will be specifically described.

Figure 22:
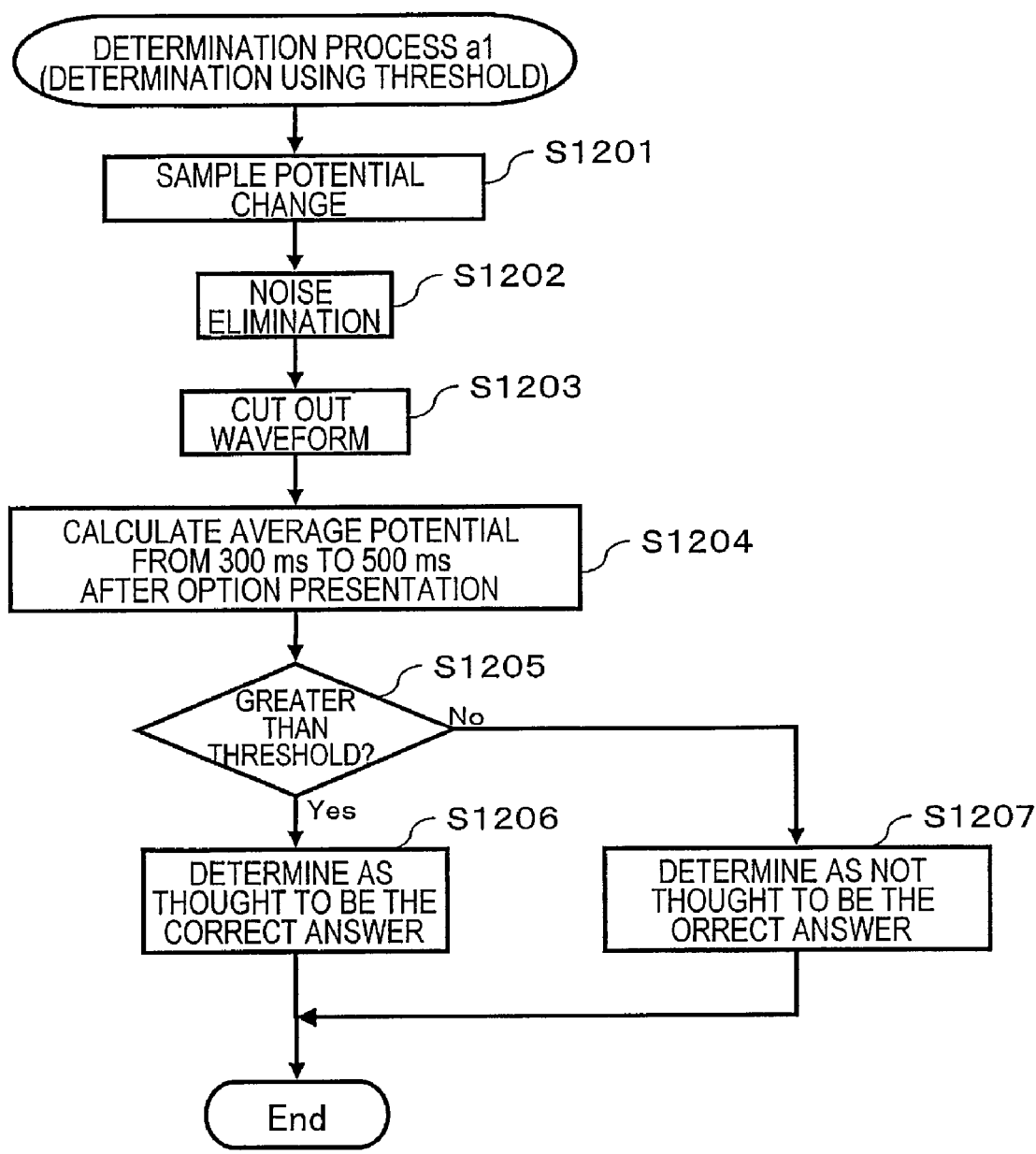
FIG. 22 A flowchart showing the procedure of a determination process a1 utilizing a threshold.

FIG. 22 shows the procedure of an option determination process a1 utilizing a threshold. In the determination process a1, an average potential at about 400 milliseconds since the point of option presentation is subjected to threshold processing in order to make a determination. Hereinafter, the steps of the process a1 will be described in order.

First, starting at the point of option presentation, a potential change of the electroencephalograms is sampled (S1201). Examples of sampling frequencies are 200 Hz, 500 Hz, and 1000 Hz, for example.

Next, noise is eliminated from the waveform of the sampled potential change (S1202). For example, in order to cut off the low-frequency and high-frequency components which are mixed in the signal, the signal is allowed to pass through a 0.16-20 Hz band-pass filter, or any sample that is fear to have noises (e.g. electroocular) mixed therein (e.g., a sample showing an amplitude of 100 μV or more on any of the electrodes) may be discarded from the subject of distinction.

Next, out of the potential change of the electroencephalograms from which noise has been eliminated, the waveform of a time slot that relates to the determination as to having thought to be the correct answer or not is cut out (S1203). From the aforementioned experimental results, it is known that the relevant time slot is at about 400 milliseconds since the point of option presentation. Therefore, 300 milliseconds to 500 milliseconds after the option presentation may be cut out, for example. As will be appreciated, the range to be cut out is not limited to the above. For example, it may be set to 200 milliseconds to 700 milliseconds after the option presentation, excluding 200 milliseconds after the option presentation, which is affected by the primary response to the option presentation.

Next, an average potential of the potentials of the respective samples of waveforms in the time slot that has been cut out is calculated (S1204).

Then, the calculated average potential is compared against a threshold (S1205). As the threshold, for example, average potentials of "thought to be the correct answer" and "thought to be not the correct answer+not sure (not thought to be the correct answer)" may respectively be calculated, and a value (e.g. an intermediate value) which lies between the calculated average potentials may be used. In the above-described experiment, the threshold which was determined from the respective average potentials of "thought to be the correct answer" and "thought to be not the correct answer+not sure (not thought to be the correct answer)" from the 11 test subjects was −0.9 μV.

If the average potential is greater than the threshold (Yes at S1205), the user determines the presented option as thought to be the correct answer (S1206). On the other hand, if the average potential is smaller than the threshold (No at S1205), the user determines it as not thought to be the correct answer (S1207).

In the case of using the process a1, the distinction ratio for "thought to be the correct answer"/"not thought to be the correct answer" was 59%. It is considered that the distinction ratio will be improved by eliminating the background electroencephalograms and noises (e.g. electroocular) with a further increased precision.

In order to perform the determination with a higher precision, other than simply subjecting an average potential to threshold processing as in the process a1, a calculated average potential and pre-generated average potentials after presenting options that are "thought to be the correct answer" and "not thought to be the correct answer" may be used for calculating a Mahalanobis distance from each group, and a determination may be made by using the Mahalanobis distances.

The Mahalanobis distance indicates a distance from the center of gravity of a group, by taking into consideration the variance and covariance of data. Therefore, a determination using the Mahalanobis distance is known to provide a higher distinction ability than making a determination through simple threshold processing. Formula 1 below shows a calculation formula for a Mahalanobis distance.

$$D_j^2 = (X - \mu_j)' \sum_j^{-1} (X - \mu_j) \qquad [\text{eq. 1}]$$

In Formula 1, X is an average potential of measured waveform; μ is a center of gravity of the average potential of a group; and Σ−1 is an inverse matrix of a covariance matrix of the average potential of the group. D2 is a square of the Mahalanobis distance between the average potential of the measured waveform and the group.

Figure 23:
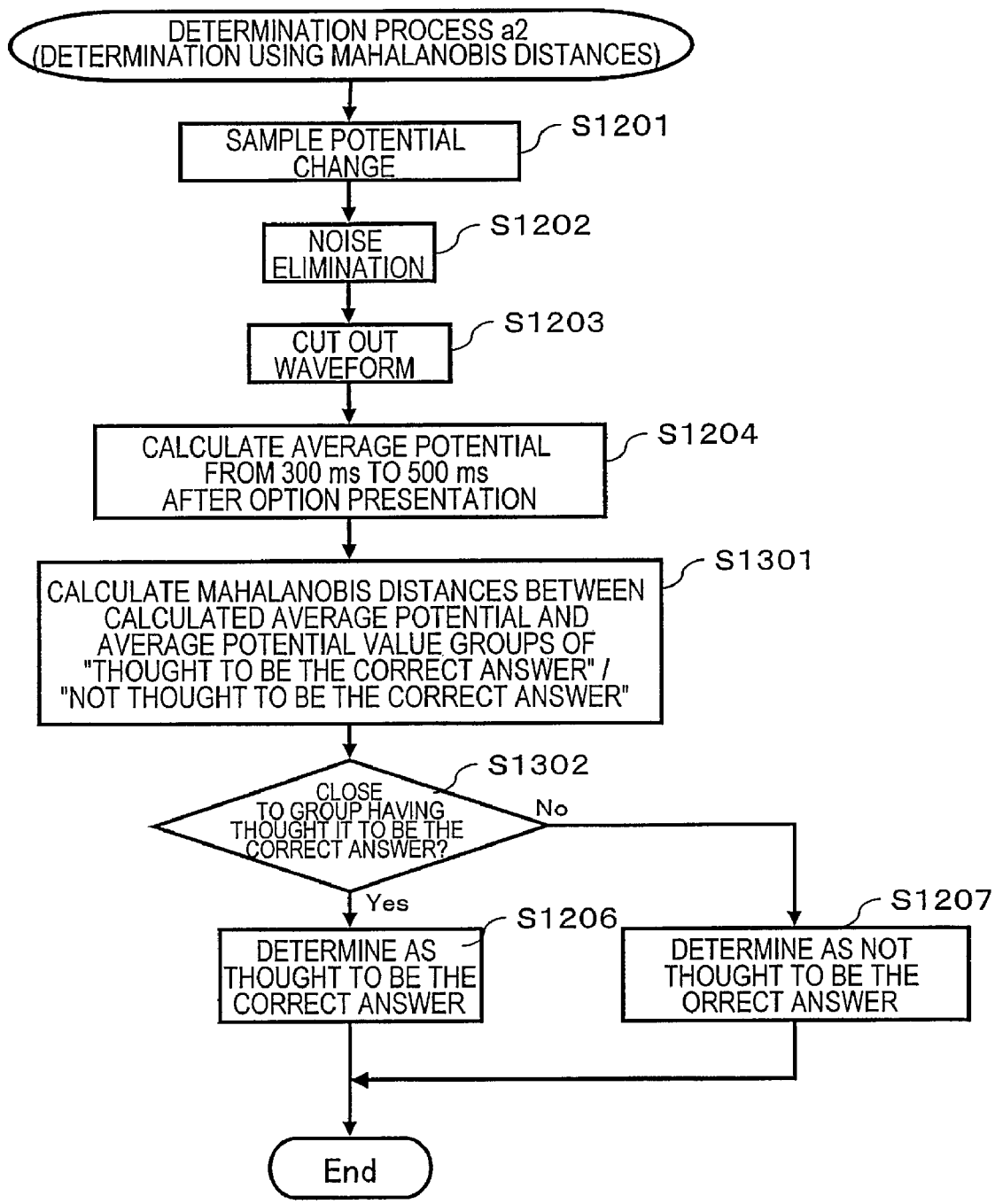
FIG. 23 A flowchart showing the procedure of a option determination process a2 utilizing Mahalanobis distances.

FIG. 23 shows the procedure of an option determination process a2 utilizing Mahalanobis distances. In addition to the aforementioned process a1 (FIG. 22), the determination process a2 calculates Mahalanobis distances. Hereinafter, the steps of the determination process a2 will be described in order. Any step where the same process as in FIG. 22 is performed is denoted by the same numeral and the description thereof is omitted.

A Mahalanobis distance between the calculated average potential and each of pre-generated "thought to be the correct answer" and "not thought to be the correct answer" groups is calculated (S1301), and the calculated Mahalanobis distances to the respective groups are compared (S1302). Then, if the distance to the "thought to be the correct answer" group is closer (Yes at S1302), a determination of having thought to be the correct answer is made (S1206). On the other hand, if the distance to the "thought to be the correct answer" group is not close (No at S1302), a determination of having not thought to be the correct answer is made (S1207).

In practice, in order to generate the "thought to be the correct answer" and "not thought to be the correct answer" groups, a preliminary investigation may be performed in advance, and an average potential of waveforms for each test of "thought to be the correct answer" or "not thought to be the correct answer" may be calculated among the users (pupils), and defined respectively as "thought to be the correct answer" and "not thought to be the correct answer" groups (average potential groups). It will be appreciated that each group may be generated with respect to individual users.

In the case of using the process a2, the distinction ratio for "thought to be the correct answer"/"not thought to be the correct answer" was 61%. It is considered that the distinction ratio will be improved by eliminating the background electroencephalograms and noises (e.g. electroocular) with a further increased precision.

Figure 24:
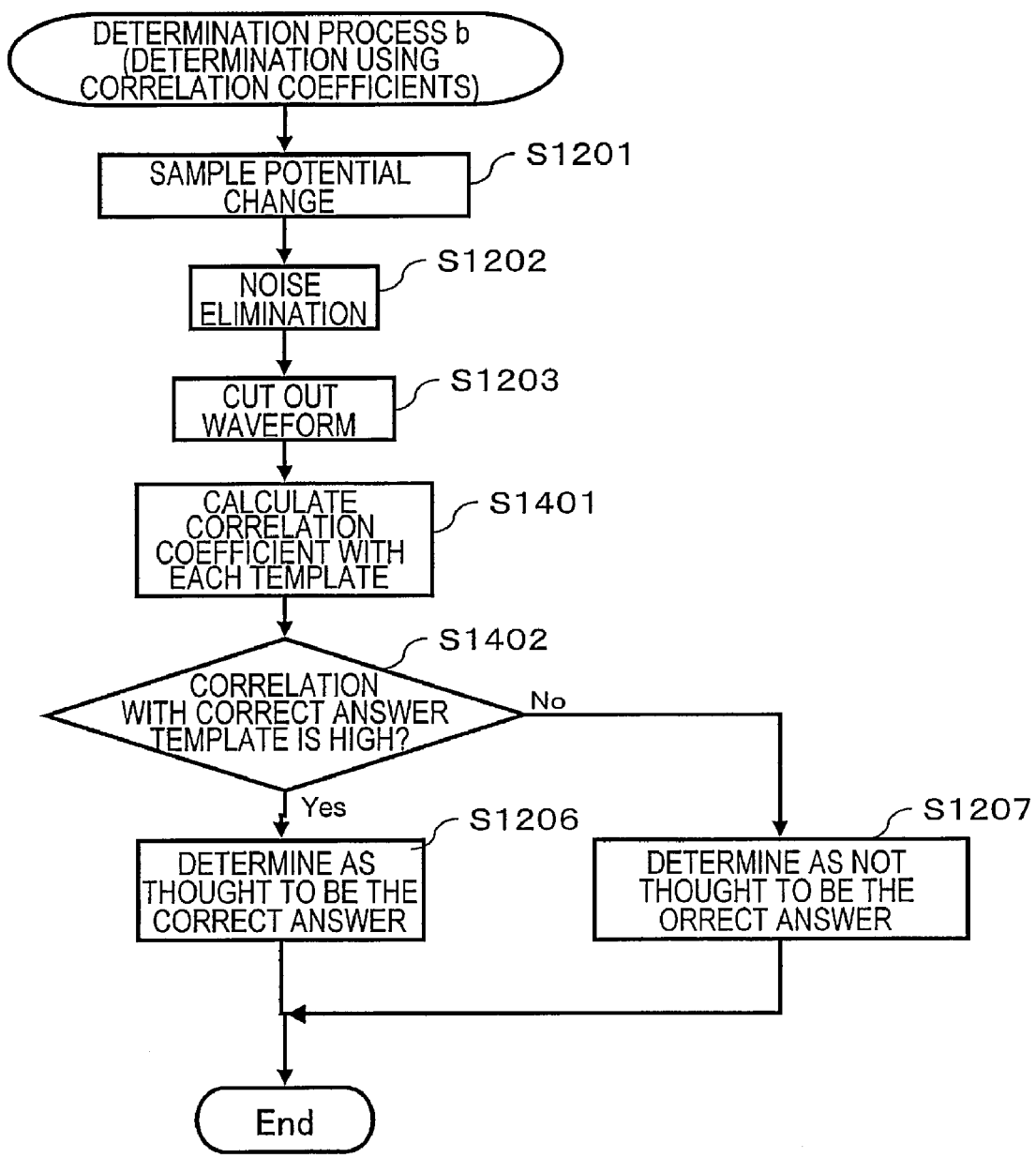
FIG. 24 A flowchart showing the procedure of an option determination process b utilizing correlation coefficients.

FIG. 24 shows the procedure of an option determination process b utilizing correlation coefficients. The determination process b makes a determination by calculating a correlation coefficient between each of a pre-generated "thought to be the correct answer" template (correct answer template) and a "not thought to be the correct answer" template (incorrect answer template) and a waveform of the time slot corresponding to the template.

The correct answer template and the incorrect answer template are each generated by cutting out waveforms in the time slot at about 400 milliseconds since the point of option presentation. Specifically, the waveforms of event-related potentials of 11 test subjects who have "thought it to be the correct answer" are cut out, and a total arithmetic mean waveform thereof is obtained and defined as a correct answer template. Moreover, the waveforms of event-related potentials of 11 test subjects who have "not thought it to be the correct answer" are cut out, and a total arithmetic mean waveform thereof is obtained and defined as an incorrect answer template.

Hereinafter, the steps of the process b will be described in order. Any step where the same process as in FIG. 22 is performed is denoted by the same numeral and the description thereof is omitted.

Correlation coefficients between the waveform of the event-related potential of the user having been cut out and the correct answer template and incorrect answer template are calculated (S1401). As a result, two correlation coefficients are obtained. Note that the method for calculating a correlation coefficient is well-known in connection with statistics and mathematical analysis. In the present specification, detailed descriptions thereof are omitted.

Next, the two correlation coefficients having been derived are compared, and if the correlation with the correct answer template is higher (Yes at S1402), it is determined that the user has thought it to be the correct answer (S1206). On the other hand, if the distance to the "thought it to be the correct answer" group is not close (No at S1302), it is determined that he or she has not thought it to be the correct answer (S1207).

In the case of using the process b, the distinction ratio for "thought to be the correct answer"/"not thought to be the correct answer" was 58%. It is considered that the distinction ratio will be improved by eliminating the background electroencephalograms and noises (e.g. electroocular) with a further increased precision.

Figure 25:
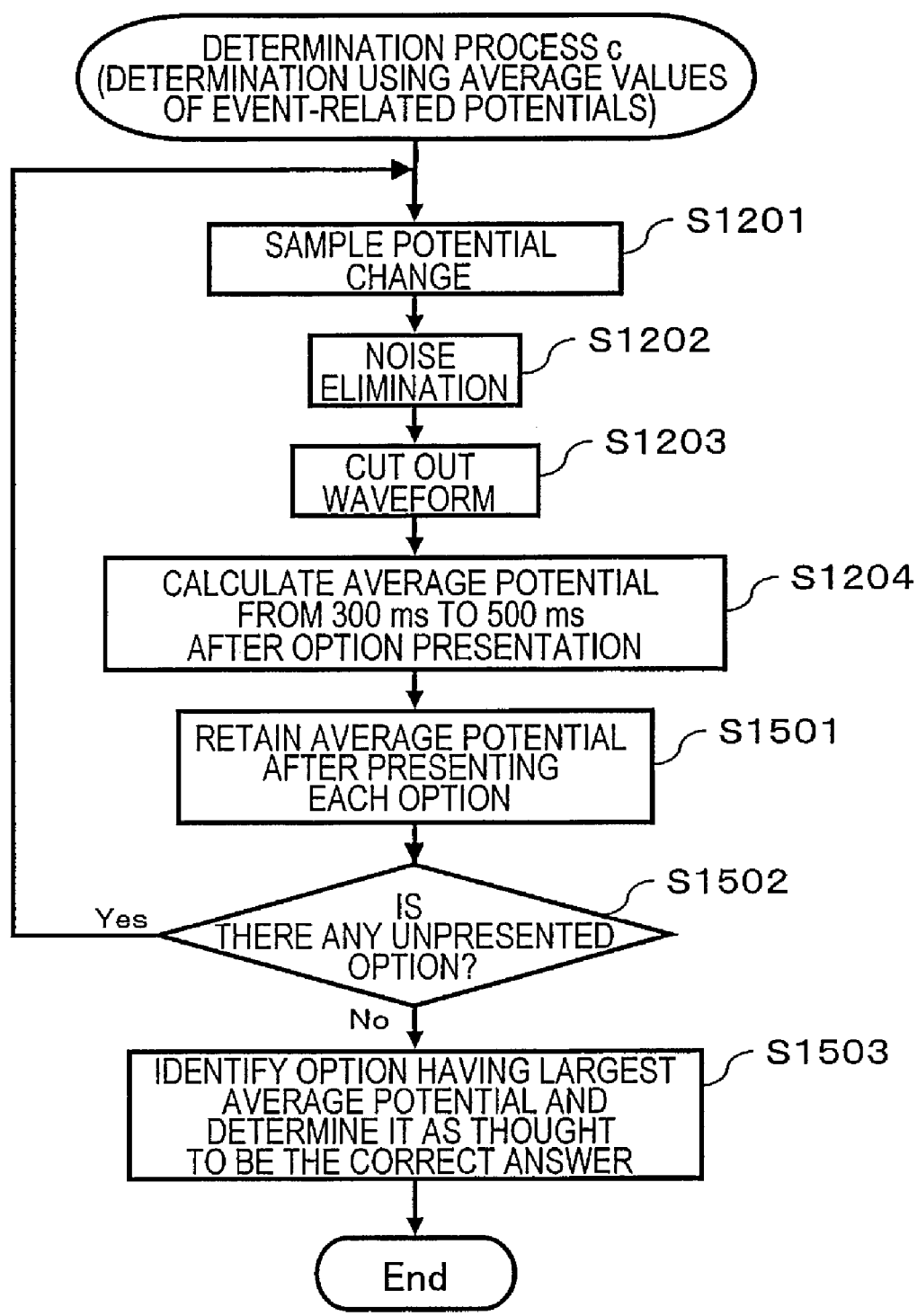
FIG. 25 A flowchart showing the procedure of an option determination process c utilizing average values of event-related potentials.

Instead of the above-described processing methods (process a1, process a2, process b), or in addition to using the above-described processing methods, other techniques may also be used. For example, FIG. 25 shows the procedure of an option determination process c utilizing average values of event-related potentials. As in this determination process c, among the options that are consecutively presented for each question, it may be assumed that the user has thought at least one to be the correct answer, and average potentials that are calculated for the respective options may be compared, and the option having the largest average potential may be determined as being thought to be the correct answer.

FIG. 25 will be briefly described. Any step where the same process as in FIG. 22 is performed is denoted by the same numeral and the description thereof is omitted.

First, a step of retaining the average potential calculated for each option is added (S1501). Next, a branching occurs depending on whether there is any unpresented option (S1502), if there is any unpresented option, the next option is presented, and the potential change is sampled by using the point of option presentation as a starting point (S1201). On the other hand, if there is no unpresented option, the average potentials of the respective options retained at step S1501 are compared, and the option having the largest average potential is identified, and this option is determined as being thought to be the correct answer (S1503).

In the case of using the process c, the distinction ratio for "thought to be the correct answer" was 60%. It is considered that the distinction ratio will be improved by eliminating the background electroencephalograms and noises (e.g. electroocular) with a further increased precision.

3. Construction of the Service Providing System According to the Present Invention The service providing system according to the present invention is able to, even in the absence of an answer input from the user, determines which option the user has thought to be the correct answer, and enables similar processing to the case where there is an answer input, by using an event-related potential of a user during study.

For example, the present service providing system presents a history or arithmetic question to a user, and thereafter sequentially presents a plurality of options which are candidate answers to that question. Then, by utilizing the waveform of the event-related potential of the user in a period at about 400 milliseconds since the point of option presentation, it is determined as to whether the user has thought the option to be the correct answer or not. By using the event-related potential, even in the absence of an answer input from the user, it is possible to automatically determine the option which the user has thought to be the correct answer in his or her mind, thereby realizing a system that is able to provide study assistance in a manner similar to when there is an answer input.

The content of study assistance may vary. For example, when an option which the user has thought to be the correct answer does not match the actual correct answer, a notice of incorrectness may be given, and the correct answer may also be presented to the user. Moreover, the user's degree of understanding may be determined from the option which the user has thought to be the correct answer and the actual correct answer, and a question to be next presented may be selected based on the degree of understanding. As a result of this, the service providing system functions as a study system which does not require the user's answering manipulation. Hereinafter, a service providing system which is implemented as a study system will be described.

First, with reference to FIG. 1, a specific example of the service providing system will be described. With reference to FIG. 2 to FIG. 8, the general construction and operation of the service providing system will be described.

FIG. 1 shows an exemplary construction of the service providing system 1 according to the present embodiment. The service providing system 1 includes a service providing apparatus 10, a biological signal detection section 100, and an output section 101 such as a display.

FIG. 1 schematically shows a manner in which a user 50 wearing the biological signal detection section 100 is using the service providing apparatus 10 and the output section 101 for studying while holding onto a hand strap on a train. In such a situation, it is difficult for the user 50 to input an answer because both hands are full.

In accordance with the service providing system 1 of the present embodiment, the service providing apparatus 10 consecutively presents to the user a question and a plurality of answer options, one by one, via the output section 101. The user 50 does not need to make any answer input, but may just be looking at the presented question and the respective options.

The service providing apparatus 10 acquires an event-related potential of the electroencephalograms of the user 50 that is measured by the biological signal detection section 100 by using the point of presenting each option as a starting point. The biological signal detection section 100 according to the present embodiment is contemplated as a head-mount type electroencephalograph, and is capable of wirelessly transmitting a detected electroencephalograms signal to the service providing apparatus 10.

Note that this electroencephalograph has electrodes placed thereon, such that, when worn on the head of the user 50, the electrodes will come in contact with predetermined positions on the head. The electrode positions are to be determined in terms of reliability of signal measurement, ease of wearing, and the like. For example, the electrodes are placed at Pz (median vertex), A1 (earlobe), and the root of nose of the user 50, as shown in FIG. 20. Alternatively, potential measurements can be made with at least two, e.g., positions Pz and A1 alone. As a result, the biological signal detection section 100 is able to measure an event-related potential of the user 50.

Based on the event-related potential at about 400 milliseconds since the point of each option presentation, the service providing apparatus 10 determines whether the user 50 thinks each option to be the correct answer or not. Then, based on whether an actually correct answer is being made or not, manners of presenting the result and selecting the next question for presentation to the user may be changed. As a result, even in the case where the user 50 does not explicitly make an answer, he or she can enjoy study assistance in a manner similar to when there is an answer input. Moreover, the user is able to study irrespective of the place or environment in which the service providing system 1 is used.

As can be understood from the above description, in the present embodiment, the service providing system 1 may be regarded as a study system or a quizzing system.

Note that, in the present specification, it is assumed that an event-related potential of a point at about 400 milliseconds as counted from a point of option presentation is utilized. Regarding the event-related potential of a user which is measured in order to determine whether an option is the correct answer or not, "about 400 ms" means a time slot in which a significant characteristic feature in the event-related potential appeared in the experiment by the inventors, and may be a period from about 350 milliseconds to about 450 milliseconds for example.

3-1. EMBODIMENT 1

3-1-1. Detailed Construction of the Service Providing System According to Embodiment 1

FIG. 2 shows a functional block construction of the service providing system 1 according to the present embodiment. FIG. 2 also shows detailed functional blocks of the service providing apparatus 10. The user block 50 is shown for convenience of description.

The service providing apparatus 10 is connected to the biological signal detection section 100 and the output section 101 in a wired or wireless manner, and performs transmission and reception of signals. Although FIG. 2 illustrates the biological signal detection section 100 and the output section 101 as separate entities from the service providing apparatus 1, this is only exemplary. Some or all of the biological signal detection section 100 and the output section 101 may be provided within the service providing apparatus 1.

The biological signal detection section 100 is an electroencephalograph which detects a biological signal from the user 50, and measures electroencephalograms as a biological signal. It is assumed that the user 50 is wearing the electroencephalograph in advance. The measure electroencephalograms of the user 50 are sampled so as to become computer-processible, and are sent to a user state determination section 200.

The output section 101 is a device which receives a signal from the service providing apparatus 10, and displays a content based on that signal, e.g., information such as a question to the user 50, answer options, or a hint. The output section 101 corresponds to the display of FIG. 1, but may also include loudspeakers and the like.

Next, the detailed construction of the service providing apparatus 10 will be described.

The service providing apparatus 10 is implemented as a computer system which executes the subsequently-described processes. The service providing apparatus 10 includes a RAM 301, a computer program 400, a central processing unit (CPU) 300, a question database (question DB) 203, and a result-storing database (result-storing DB) 204.

By executing the computer program 400 stored in the RAM 301, the CPU 300 realizes functions in accordance with the processing procedure of the program. In the present embodiment, the CPU 300 operates as the user state determination section 200 and the selection section 205. Hereinafter, the functions of the selection section 205 will be further subdivided, so as to be discussed separately as a question-for-presentation selection section 201 for selecting a question to be presented to the user and an option-for-presentation selection section 202 for selecting a plurality of options in a predetermined order as candidate answers to that question.

The computer program 400 to be utilized may be a single program, or may be two or more different programs. The computer program is in the form of a product which is recorded on a storage medium, e.g., an optical disk such as a CD-ROM or a semiconductor memory such as a memory card, and distributed on the market, or transmitted through telecommunications lines, e.g., the Internet. Note that the user state determination section 200, the question-for-presentation selection section 201, and the option-for-presentation selection section 202 may also be realized by hardware means, e.g., a DSP, that comprises semiconductor circuitry in which a computer program is incorporated.

The question DB 203 stores data concerning questions, e.g., questions, options, correct answers, importance levels of the questions, and genres of the questions. FIGS. 3(*a*) and (*b*) show specific examples of data concerning questions stored in the question DB 203. A "question" column indicates question numbers and questions. An "option" column contains sets of an alphabet letter for an option name and the content of the option, according to the number of options (e.g. 4).

Note that each option has a content that is immediately recognizable to the test subject, i.e., not any lengthy content which requires time to read or any character or content that is difficult for the user to understand. As a result, it can be assumed that recognition is completed substantially simultaneously with the presentation of an option, and it can be determined as to whether the user has thought the option to be the correct answer or not by measuring the event-related potential at about 400 milliseconds as counted from a point of option presentation. However, in the case where the service providing apparatus 10 is able to accurately detect completion of recognition and identify the event-related potential at about 400 milliseconds as counted from the point of detection, the content does not need to be immediately recognizable to the test subject.

Although the present specification illustrates the question DB 203 as being internalized in the service providing apparatus 10, this is exemplary. The question DB may be provided on a storage medium (e.g., a memory card or optical disk) which is removable from the service providing apparatus 10, for example. This also applies to the result-storing DB 204 described later. The storage medium storing the question DB 203 and/or result-storing DB may further contain the aforementioned computer program.

The question-for-presentation selection section 201 selects a question to be next presented by referring to the question DB 203, and presents only the question via the output section 101. The time during which the question is presented to the user 50 may be e.g. 10 seconds in order to allow for the time needed by the user 50 to understand the content of the question and think up a correct answer, or may be individually set based on the difficulty level, number of characters, etc., of the question.

Moreover, while referring to the determination result stored in the result-storing DB 204 as to whether the user has thought the option to be the correct answer or not, the question-for-presentation selection section 201 selects a question to be next presented by referring to the question DB 203. The manner of determining the next question will be specifically described after the description of the determination result DB 204.

By referring to the question DB 203, the option-for-presentation selection section 202 selects answer options for the question selected by the question-for-presentation selection section 201, one by one, as in step 2 to step 5 in FIG. 18, and presents them via the output section 101. The time during which to present the answer option may be e.g. 1 second in order to allow for the time needed by the user 50 to confirm the content of the answer option, or may be set in accordance with the option. However, an interval of at least about 500 milliseconds must be observed because an event-related potential at about 400 milliseconds since the point of option presentation as a starting point is to be used.

After all options are presented for each question, the option-for-presentation selection section 202 presents the correct answer (option) via the output section 101 by referring to the question DB 203. Note that the option-for-presentation selection section 202 may newly refer to the determination result stored in the result-storing DB 204 described later, and feed back correctness of the option which the user 50 has thought to be the correct answer against the actual correct answer which is described in the question DB 203.

The user state determination section (hereinafter referred to as the "determination section") 200 has a function of receiving sampled electroencephalograms of the user 50 from the biological signal detection section 100, and determining whether the user 50 has thought the option to be the correct answer or not, by using a portion of the event-related potential at about 400 milliseconds since the timing at which the option is output via the output section 101 as a starting point.

Various methods are possible for making a determination as to having thought to be the correct answer.

For example, an average potential of the event-related potential at about 400 milliseconds since the point of option presentation is compared against a previously determined threshold. If the average potential is greater than the threshold, a determination of having "thought to be the correct answer" is made; and if it is smaller than the threshold, a determination of having "not thought to be the correct answer" is made.

As this threshold, −0.9 μV, which is calculated from the above-described event-related potential measuring experiment in a studying situation, can be used. Alternatively, a preliminary investigation may be performed in advance to measure the event-related potential during study, and a value obtained by averaging out the respective average potentials of "thought to be the correct answer" and "not thought to be the correct answer" of the users (pupils) may be used, or it may be ascertained for each individual. This threshold is stored in a memory (not shown) of the determination section 200, for example.

Moreover, since it is presumable that there are individual differences in the respective average potentials of "thought to be the correct answer" and "not thought to be the correct answer", a calibration may be performed for each user to identify the average potentials. The service providing apparatus 10 may perform a calibration as follows, for example.

That is, when the question-for-presentation selection section 201 presents a very easy question having an obvious correct answer (e.g., an arithmetic calculation of one digit+ one digit), the option-for-presentation selection section 202 selects one correct option and one or more incorrect options in an arbitrary order, and causes them to be presented via the output section 101. Then, the determination section 200 may determine the threshold by utilizing, as the average potential for "thought to be the correct answer" and the average potential for "not thought to be the correct answer", the respective average potentials when the correct option and the incorrect option(s) are presented. Alternatively, the system may be allowed to study the determined threshold, and the threshold may be updated as appropriate. This threshold is retained in a memory (not shown) of the determination section 200, for example.

The timing for the service providing apparatus 10 to perform a calibration is when the service providing system 1 begins to be used (i.e., when powering the service providing apparatus 10) or when a calibration instruction is received from the user, for example.

As another determination method, the determination section 200 may calculate Mahalanobis distances to make a determination between "thought to be the correct answer"/"not thought to be the correct answer". When adopting this determination method, a table to serve as a reference is used. For example, FIG. 4 shows an example of a reference table 210 for calculating Mahalanobis distances. The reference table 210 is generated so as to store respective average potential values of a "thought to be the correct answer" group and a "not thought to be the correct answer" group as obtained through a preliminary investigation. This reference table is stored in a memory (not shown) of the determination section 200.

The determination section 200 determines a Mahalanobis distance between the calculated average potential of the user and the pre-generated "thought to be the correct answer" group and a Mahalanobis distance between that average potential and the "not thought to be the correct answer" group.

A Mahalanobis distance can be determined according to eq. 1 above. The determination section 200 compares the determined Mahalanobis distances against each other, and if the Mahalanobis distance from the "thought to be the correct answer" group is smaller than the Mahalanobis distance from the "not thought to be the correct answer" group, a determination of having "thought to be the correct answer" is made, and if larger, a determination of having "not thought to be the correct answer" is made.

As still another determination method, the determination section 200 may respectively determine a correlation coefficient with the "thought to be the correct answer" template that has been pre-generated with regard to the event-related potential of the user 50 and a correlation coefficient with the "not thought to be the correct answer" template. Then, the determined correlation coefficients are compared against each other. If the correlation with the "thought to be the correct answer" template is higher, a determination of having "thought to be the correct answer" is made; and if it is lower, a determination of having "not thought to be the correct answer" is made.

As still another determination method, for each question, the determination section 200 may make a comparison of the average potentials, Mahalanobis distances, or correlation coefficients of the respective options as stored in the result-storing DB 204. Then, an option having the largest average potential, an option having the shortest Mahalanobis distance from "thought to be the correct answer", or an option having the highest correlation coefficient with the "thought to be the correct answer" template may be determined as being "thought to be the correct answer". When adopting this determination method, one of the options will always be determined as an option which is thought to be the correct answer.

The result-storing DB 204 stores the result of determination by the determination section 200. FIG. 5 shows an exemplary data structure of the result-storing DB 204. As in FIG. 5, for each option, for example, 1 may be stored when a determination of having "thought to be the correct answer" is made by the determination section 200, 0 when a determination of having "thought to be not the correct answer" is made, −1 when it is excluded from determination due to mixing of noises (e.g. electroocular), and so on.

Now, a method by which the aforementioned question-for-presentation selection section 201 selects a question to be next presented by utilizing the question DB 203 and the result-storing DB 204 will be described.

Based on the correct answer option stored in the question DB 203 and the determination result stored in the result-storing DB 204 as to whether the user has thought the option to be the correct answer or not, the question-for-presentation selection section 201 selects a question to be next presented, by using a table which describes selection rules.

FIG. 6 shows an exemplary data structure of the question-for-presentation selection rule table 211. When asking a 4-choice question, for example, the question-for-presentation selection rule table 211 is utilized for determining the genre of the next question based on the relationship between the actually correct answer option that is described in the question DB 203 and the determination result as to having thought to be the correct answer or not that is stored in the result-storing DB 204. The given question can be determined as being understood only if the number of options having been determined as "thought to be the correct answer" that is stored in the result-storing DB 204 is one and that option matches the actually correct answer option. Therefore, the rules are described in such a manner that a question from another genre will be selected as the next question in this case.

For example, in the question DB 203 shown in FIG. 3(b), a genre "addition 2" is provided next to a genre "addition 1". Based on the question-for-presentation selection rule table 211, the question-for-presentation selection section 201 is able to select from the question DB 203 a genre which is in accordance with the progress of study. The progress of study can be determined based on the result-storing DB 204.

Moreover, FIG. 7 shows another exemplary data structure of the question-for-presentation selection rule table 211. The table 211 can be utilized together with the question DB 203 shown in FIG. 3(a) and the result-storing DB shown in FIG. 5.

The question-for-presentation selection section 201 retains the question-for-presentation selection rule table in an internal or external storage device, and is able to perform a process of selecting a question based on these selection rules.

The above-described method of assisting in study by using the correct answers to questions stored in the question DB 203 and the determination results stored in the result-storing DB 204 are only exemplary. This method is similar to the case where there is an answer input made, and various other methods are conceivable.

3-1-2. Processing by the Service Providing System According to Embodiment 1

Next, with reference to a flowchart of FIG. 8, an overall flow of processes to be performed by the service providing system 1 of FIG. 2 will be described.

FIG. 8 shows a procedure of processing by the service providing system 1. This procedure is an example where a 4-choice question is presented.

At step S101, the question-for-presentation selection section 201 selects a question to be first presented from among the questions stored in the question DB 203. The method of selecting the question may be, as shown in FIG. 3 for example, in descending order of importance levels of the questions stored in the question DB 203.

At step S102, the output section 101 presents the question which has been selected by the question-for-presentation selection section 201 at step 101 to the user 50. At step S102, the time during which to present the question to the user 50 may be e.g. 10 seconds in order to allow for the time needed by the user 50 to understand the content of the question, or may be individually set based on the difficulty level, number of characters, and the like of the question.

At step S103, the option-for-presentation selection section 202 initializes the number of the option. Herein, n is a number of an option such that, when n=1, option n represents a corresponding option such as option A or option 1.

At step S104, the option-for-presentation selection section 202 outputs option n via the output section 101. Moreover, at the same timing as the outputting of option n, it sends a trigger for an event-related potential to the determination section 200. Moreover, at step S104, the time during which to present the answer option may be e.g. 1 second in order to allow for the time needed by the user 50 to confirm the content of the answer option, or may be set in accordance with the option. However, an interval of at least about 500 milliseconds must be observed because an event-related potential at about 400 milliseconds since the point of option presentation as a starting point is to be used.

At step 105, from the waveform of the event-related potential at about 400 milliseconds since a starting point which is the trigger received at step S104, the determination section 200 determines whether the user 50 has thought the presented option to be the correct answer or not.

At step 106, the determination section 200 stores the result determined at step 105 to the result-storing DB 204.

At step S107, the option-for-presentation selection section 202 increments the number n of the option.

At step S108, the option-for-presentation selection section 202 determines whether n is 5 or not. If n is not 5, i.e., n is 4 or less, the process proceeds to step S104; if n is 5, the process proceeds to step S109.

Note that a determination as to whether n is 5 or not is made because the process shown in FIG. 8 contemplates a 4-choice question. In the case of a 3-choice question or a 5-choice question, for example, it may be changed to whether n is 4 or not, or whether n is 6 or not, respectively.

At step S109, the option-for-presentation selection section 202 outputs a correct answer which is described in the question DB 203 via the output section 101. Alternatively, it may newly refer to the determination result stored in the result-storing DB 204, and feed back correctness of the option which the user 50 has thought to be the correct answer against the actual correct answer described in the question DB 203.

At step S110, based on the correct answer described in the question DB 203 and the determination result stored in the determination result-storing DB 204, the question selection section 201 selects a next question, according to criteria as in the table shown in FIG. 6, for example.

At step S111, the service providing apparatus 10 determines whether or not the study questions should continue to be presented. The determination as to whether or not to continue the study may be made from the duration of the study, for example. Moreover, the user 50 may press power for the service providing apparatus 10 to thus indicate his or her own will as to whether or not to continue the study service to the providing apparatus 10. In the case whether the study is not to be ended, the process returns to step S102, and the question selected at step S110 is presented to the user 50. When the study is to be ended, the study is ended, and power to the service providing apparatus 10 is terminated.

Thus, in accordance with the service providing system 1 of the present embodiment, the service providing system 1 is constructed by using the service providing apparatus 10. Therefore, even when the user does not make an answer input, it is possible to determine which option a user has thought to be the correct answer, by using a portion of the event-related potential at about 400 milliseconds since the point of option presentation. As a result, there is realized a study system which is capable of providing study assistance in a manner similar to when there is an answer input. Therefore, by a method of appropriately selecting the genre of questions depending on the studying situation or the like, a study without answer inputs is made possible, which results in a high efficiency of studying.

3-2. EMBODIMENT 2

3-2-1. Detailed Construction of a Service Providing System According to Embodiment 2

Next, a service providing system and a service providing apparatus according to Embodiment 2 of the present invention will be described.

In the service providing system 1 according to Embodiment 1, the time during which to present a question or an answer option to a user is set in accordance with the number of characters and the difficulty level to distinguish the question or the option, for example, so as to allow the user 50 to understand and confirm the content of the question and answer options. However, even given the same question, the time until thinking up the correct answer will differ depending on the user, thus resulting in the feeling of being too late or too early relative to the timing of presenting the first option.

For example, under a setting such that the first option is to be presented in 10 seconds after a question is presented, for user A who took 5 seconds of time until thinking up the correct answer after the question was presented and user B who took 15 seconds, for example, problems may possibly occur in that the timing of presenting options is so late that efficient study cannot be performed, and that the timing of presenting options is so early that studying is hindered because the question is not understood, respectively.

Therefore, in the service providing system of the present embodiment, it is determined based on the event-related potential of electroencephalograms as to whether the user is in a state of waiting for a first option (hereinafter referred to as a waiting state) or not, and the timing of presenting options is changed in accordance with the user's waiting state.

The determination as to whether the user is in a waiting state or not is made by using the contingent negative potential (CNV: Contingent Negative Variation) of the event-related potential. The CNV component is a mild negative potential which is recorded in a state of waiting for an imperative stimulus after a preannounced stimulus, and is supposed to be strongly related to psychological factors such as anticipation, attention, volition, and motivation (see for example, Shinichi NIWA, Noriko TSURU: "JISHOKANRENDENI JISHO-KANRENDENI TO SHINKEIJYOHOUKAGAKU NO HATTEN (or 'event-related potential event-related potential and developments in neuroinformation science')", Shinkoh Igaku Shuppan, 1997, cf. P189).

The CNV component appears in a time slot before the point of option presentation (0 millisecond) in FIG. 3, indicated as the zone 34. In other words, the waveform 31, the waveform 32, and the waveform 33 are all similarly shifted in the negative direction, indicative of the presence of a CNV component. In the aforementioned event-related potential measuring experiment, each option was presented in 1 second after the test subject had pressed the space key. Therefore, it can be said that the test subject was not in a state of solving the question, but was in a waiting state for an option to be presented. The fact that the CNV component appeared in a time slot before the point of option presentation (0 millisecond) and in connection with being in a waiting state for an option to be presented indicates that, based on the CNV component as an index, it is possible to determine whether the user 50 is in a waiting state for a next presentation or not.

Note that the timing of options to be consecutively presented is also changed by considering the fact that the time for confirming an option differs from user to user.

Figure 9:
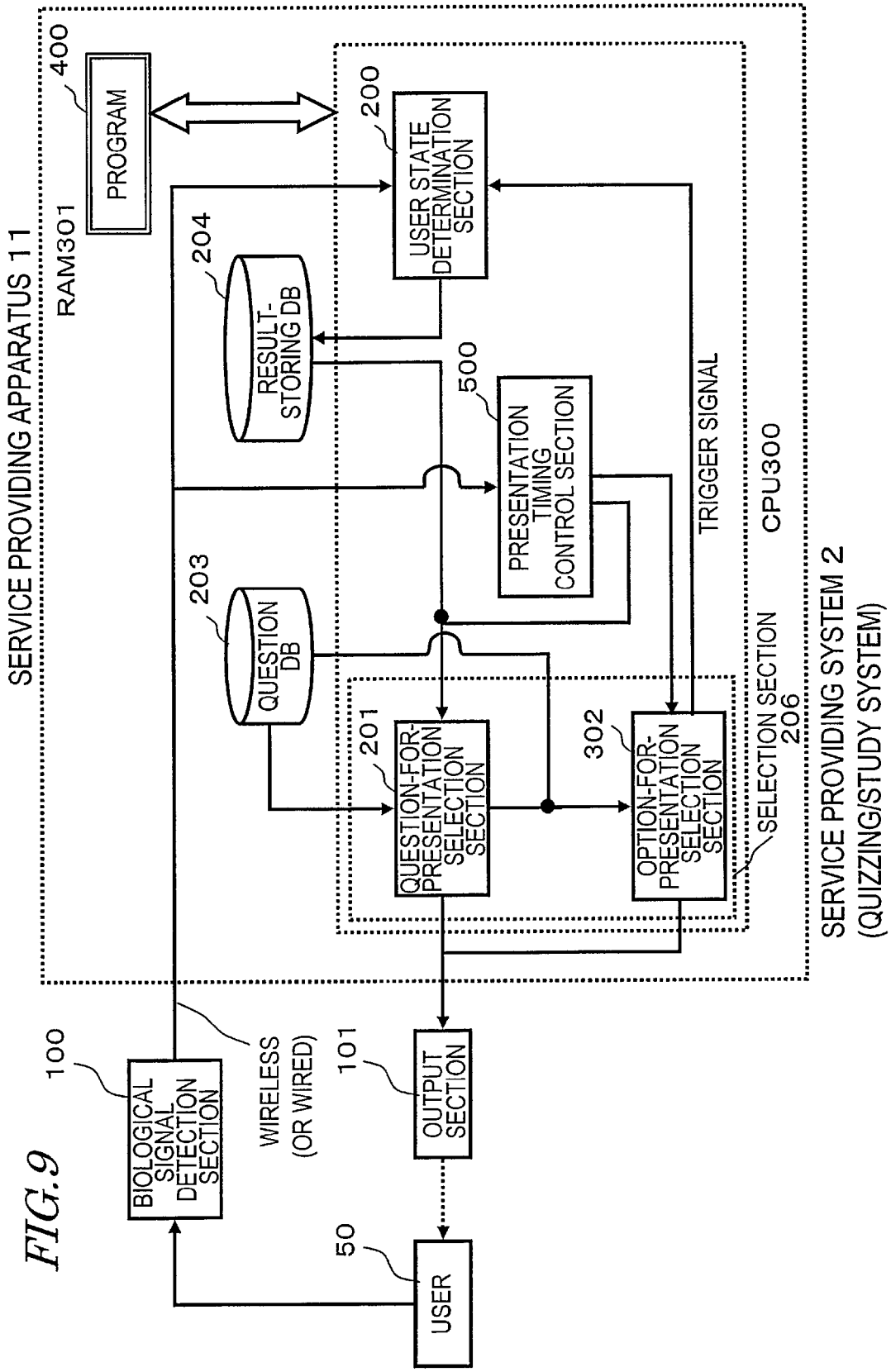
FIG. 9 A diagram showing the functional block construction of a service providing system 2 according to Embodiment 2.

FIG. 9 shows a functional block construction of the service providing system 2 according to the present embodiment. FIG. 9 also shows detailed functional blocks of the service providing apparatus 11. Note that the user block 50 is shown for convenience of description.

In FIG. 9, any component element which is the same as that in FIG. 2 is denoted by the same numeral and the description thereof is omitted. The service providing apparatus 11 shown in FIG. 9 differs from the service providing apparatus 10 shown in FIG. 2 in that a presentation timing control section 500 is comprised, which determines whether or not the user 50 in a waiting state for a next option to be presented and controls the timing for presenting questions and options.

Note that the option-for-presentation selection section 302 differs from the option-for-presentation selection section 202 in that a signal from the presentation timing control section 500 is received, and presents an option with a timing based on that signal. Otherwise, the processing is identical. The selection section 206 differs from the selection section 205 (FIG. 2) only in terms of whether the option-for-presentation selection section 302 is comprised or the option-for-presentation selection section 202 is comprised. Note that, since the content of the CPU 300 is unchanged, the same reference numeral is assigned thereto.

Hereinafter, the presentation timing control section 500 will be described.

The presentation timing control section 500 receives the sampled electroencephalograms of the user 50 from the biological signal detection section 100, and in order to allow for the time needed to understand and confirm the question or option, determines whether a CNV component of the event-related potential appears or not at e.g. 500 milliseconds from the point of presentation of the question or option as a starting point. This corresponds to a time slot before presentation of a next question. If a CNV component of the event-related potential appears, it is determined that the user 50 is in a waiting state for a next option, and a signal is sent to the option-for-presentation selection section 202 so as to present a next option.

Upon receiving the signal from the presentation timing control section 500, the option-for-presentation selection section 202 selects a next option, and presents it via the output section 101.

As mentioned earlier, the CNV component is a mild negative potential which is recorded in a state of waiting for an imperative stimulus (waiting state) after a preannounced stimulus, and is supposed to be strongly related to psychological factors such as anticipation, attention, volition, and motivation. In the aforementioned event-related potential measuring experiment, each option was presented in 1 second after the test subject had pressed the space key. Therefore, it can be said that the test subject was not in a state of solving the question, but was in a waiting state for an option to be presented. In the total arithmetic mean waveform shown in FIG. 21, three waveforms are all shifted in the negative direction in a time slot before the point of option presentation (0 millisecond) and in connection with being in a waiting state for an option to be presented. This fact also indicates that, based on the CNV component as an index, it is possible to determine whether the user 50 is in a waiting state for a next presentation or not.

The presence or absence of a CNV component may be determined by, for example, calculating a gradient from the potential waveform of the electroencephalograms of the user 50 by using a least-squares method or the like in a time period of about 500 milliseconds, and comparing it against a certain threshold. If the gradient of the waveform is smaller than the threshold, it is determined that there is a CNV component exists; if the gradient is larger, it is determined that no CNV component exists. The time period is not limited to 500 milliseconds, but may be 300 milliseconds, 700 milliseconds, 1000 milliseconds, and so on. Moreover, the threshold may be e.g. $-10 \mu V/s$ as calculated from the waveform shown in FIG. 21, or may be determined by performing a preliminary experiment for each user.

3-2-2. Processes in the Service Providing System According to Embodiment 2

Next, with reference to the flowchart of FIG. 10, the overall flow of processes performed in the service providing system 2 of FIG. 9 will be described.

Figure 10:
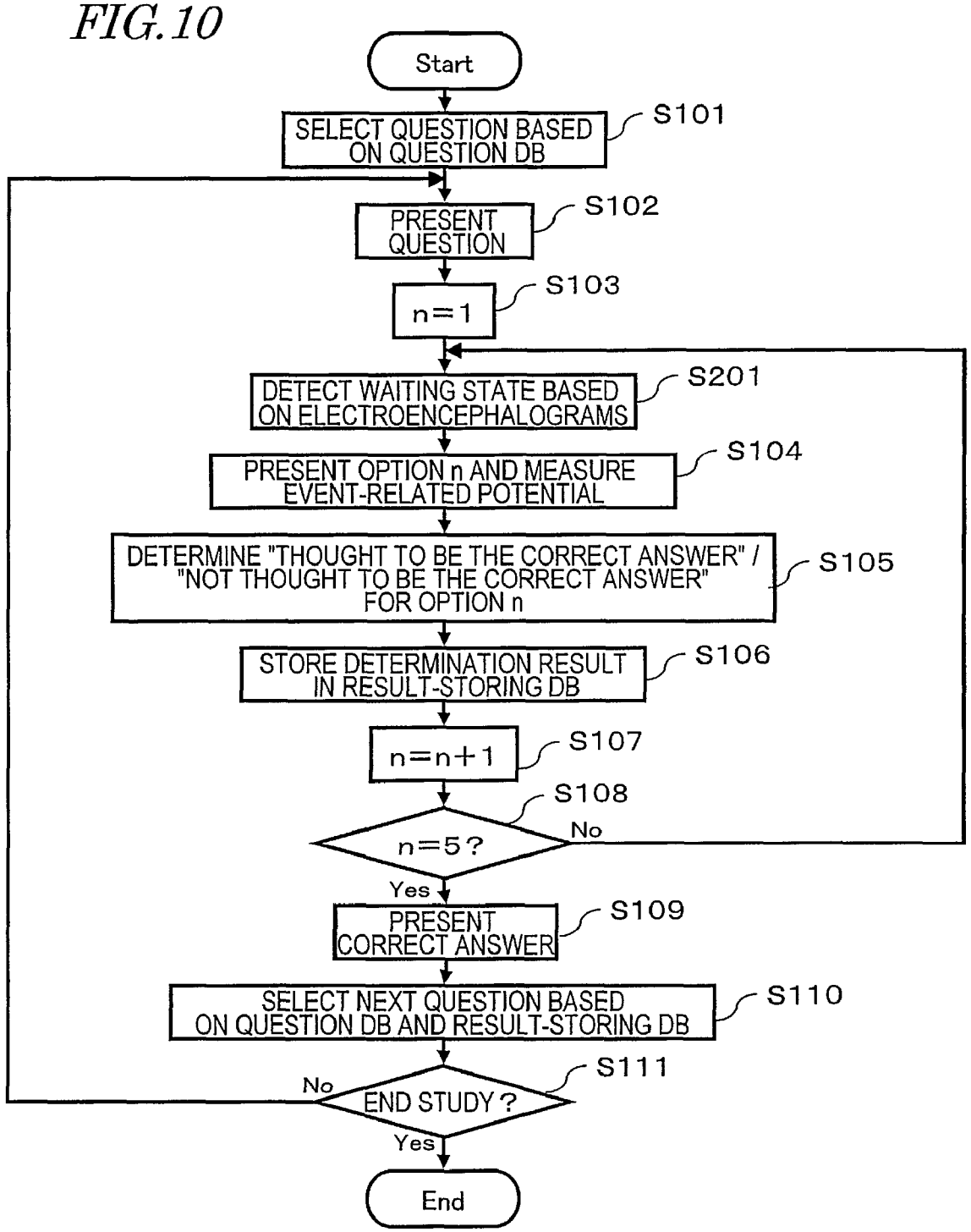
FIG. 10 A flowchart showing a procedure of processing by the service providing system 2 according to Embodiment 2.

FIG. 10 shows a procedure of processing by the service providing system 2 according to the present embodiment. This procedure shows an example when presenting a 4-choice question. Any step where the same process as in FIG. 8 is performed is denoted by the same numeral and the description thereof is omitted. First, step S101 to step S111 are identical to the processing of FIG. 8.

At step S201, the presentation timing control section 500 detects the user's 50 waiting state for presentation of a next option. If he or she is in a waiting state, the presentation timing control section 500 sends a signal to the option-for-presentation selection section 202 so as to present a next option. Upon receiving the signal, the option-for-presentation selection section 202 selects a next option, and outputs it via the output section 101 (step S104). Note that, if no CNV component appears even after 20 seconds or more, for example, a next option may be presented, or the study may be aborted by assuming that the user 50 is not concentrating on studying.

Note that, the timing for presenting a next question may also be determined by using a CNV component.

In accordance with the service providing system 2 of the present embodiment, the service providing system 2 is constructed by using the service providing apparatus 11. Therefore, it is possible to determine whether or not the user is in a waiting state for a next option to be presented by using a CNV component of the event-related potential, so that options will be presented to the user with appropriate timing.

In addition, even when the user does not make an answer input, it is possible to determine which option the user has thought to be the correct answer by using a portion of the event-related potential at about 400 milliseconds since the point of option presentation. As a result, there is realized a study system which is capable of providing study assistance in a manner similar to when there is an answer input. Therefore, a study without answer inputs is made possible, which results in a high efficiency of studying.

3-3. EMBODIMENT 3

3-3-1. Detailed Construction of the Service Providing System According to Embodiment 3

Next, a service providing system and a service providing apparatus according to Embodiment 3 of the present invention will be described.

The service providing system 1 of Embodiment 1 is arranged so that questions and answer options are all consecutively presented, in order to determine an option which the user has thought to be the correct answer by using the event-related potential and without an answer input. Therefore, depending on the number of options, a long time may be required for one question.

In the service providing system 3 of the present embodiment, a user state determination section (hereinafter "determination section") 600 notifies to an option-for-presentation selection section 601 that there is an option which has been determined as being "thought to be the correct answer", and ensures that no unnecessary subsequent answer options are presented for that question, thus realizing a more efficient study assistance.

Figure 11:
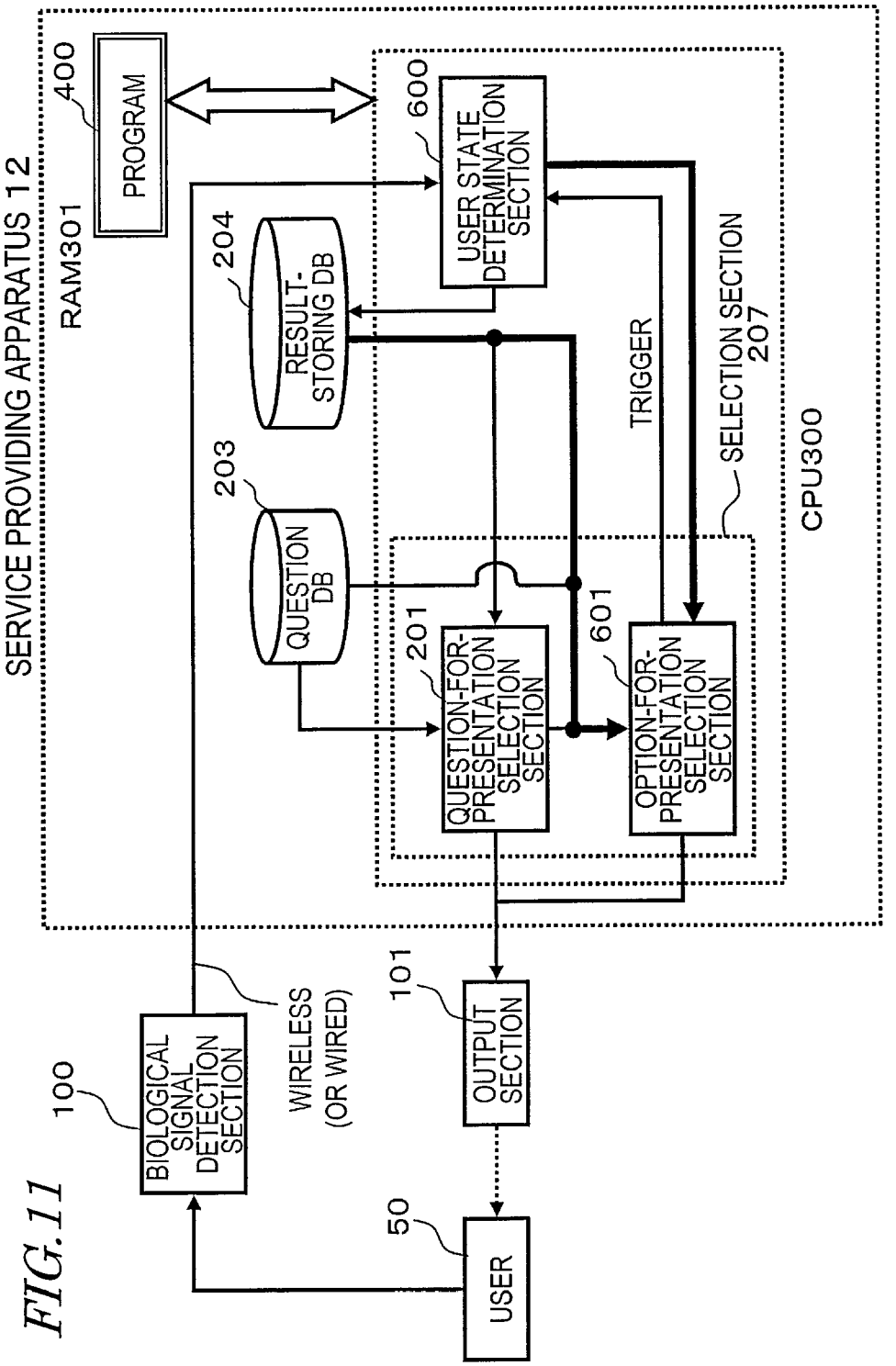
FIG. 11 A diagram showing the functional block construction of a service providing system 3 according to Embodiment 3.

FIG. 11 shows a functional block construction of the service providing system 3 according to the present embodiment. FIG. 11 also shows detailed functional blocks of the service providing apparatus 12. Note that the user block 50 is shown for convenience of description.

In FIG. 11, any component element which is the same as that in FIG. 2 is denoted by the same numeral and the description thereof is omitted. The service providing apparatus 12 shown in FIG. 11 differs from the service providing apparatus 10 shown in FIG. 2 in that the determination section 600 is comprised, which has the function of notifying an option that has been determined as being "thought to be the correct answer" to the option-for-presentation selection section 601, in addition to the functions of the determination section 200 in FIG. 2.

Note that the option-for-presentation selection section 601 differs from the option-for-presentation selection section 202 in that the option-for-presentation selection section 601 has a function of, once receiving a notice from the determination section 600, not selecting any subsequent answer options for that question. Moreover, similarly to the option-for-presentation selection section 202, after option presentation, the option-for-presentation selection section 601 presents a correct answer (option) and a result of correctness as to whether the option which the user 50 has thought to be the correct answer is the correct answer or not, for example. Otherwise, the processing is identical. The only difference between the selection section 207 and the selection section 205 (FIG. 2) is whether the option-for-presentation selection section 601 is comprised or the option-for-presentation selection section 202 is comprised. Note that, since the content of the CPU 300 and the result-storing DB 204 is unchanged, the same reference numerals are assigned thereto.

Hereinafter, the determination section 600 and the option-for-presentation selection section 601 will be described.

In addition to the aforementioned determination section 200, the determination section 600 gives a notice to the option-for-presentation section 601 when making a determination of having "thought to be the correct answer". Upon receiving this notice from the determination section 600, the option-for-presentation selection section 601 ensures that no subsequent answer options are presented. When this method is adopted, the method (process c) of later comparing the waveforms for the respective options and selecting one option that has been thought to be the correct answer cannot be used.

Since no options are presented after making a determination of having "thought to be the correct answer", the threshold for determination may be made more stringent than in the case of the determination section 200 described above, in order to make a distinction with a higher precision.

Moreover, it is conceivable that noises (e.g. electroocular) are mixed in the event-related potential, thus hindering an accurate determination. In such a case, the determination section 200 may quit the determination as to whether the user thinks the presented option to be the correct answer or not, and notify to the selection section-for-presentation presentation section 601 that it has been excluded from determination. Upon receiving this notice, the selection section-for-presentation presentation section 601 may again present that option.

3-3-2. Processes in the Service Providing System According to Embodiment 3

Next, with reference to the flowchart of FIG. 12, the overall flow of processes performed in the service providing system 3 of FIG. 12 will be described.

Figure 12:
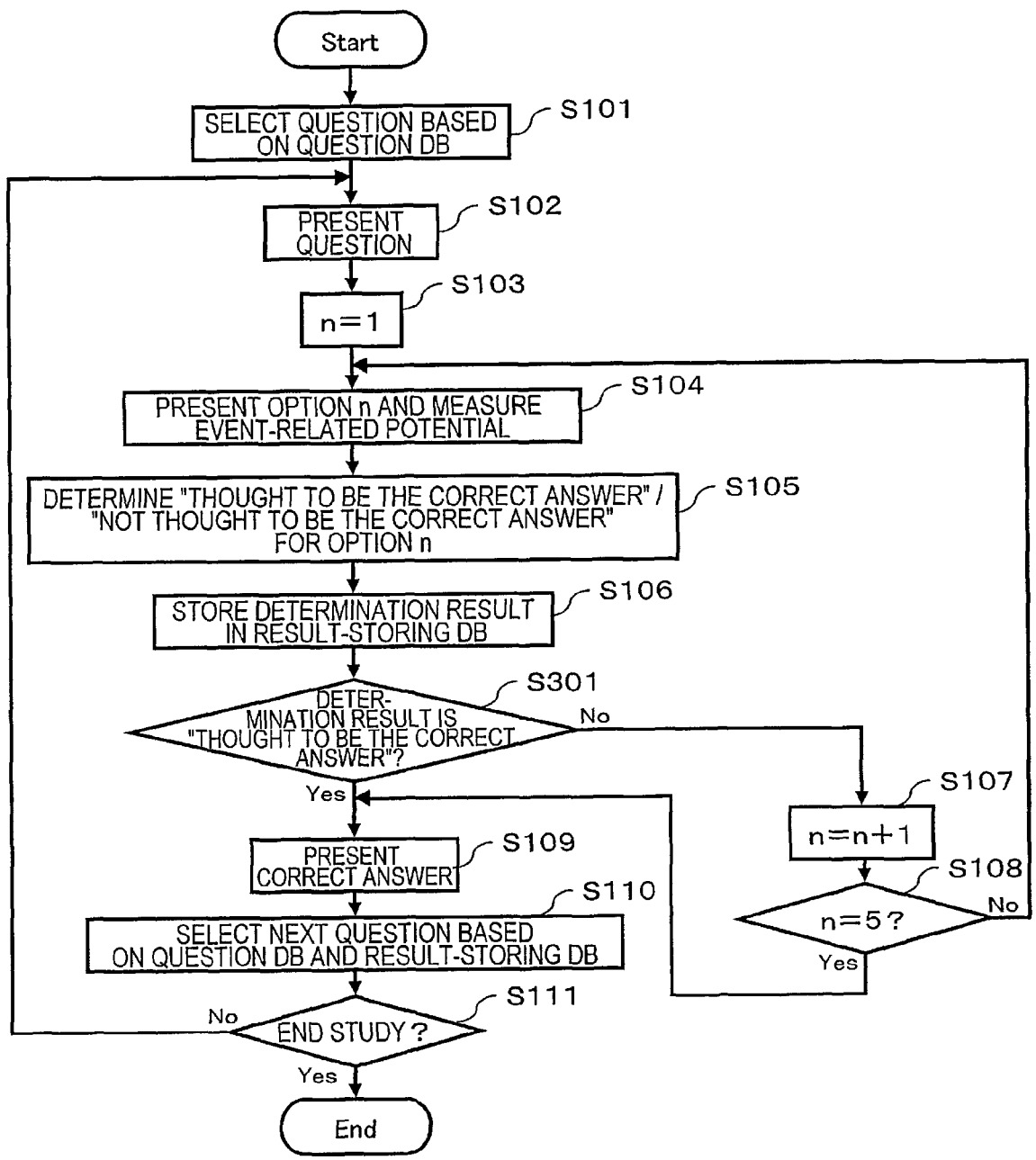
FIG. 12 A flowchart showing a first procedure of processing by the service providing system 3 according to Embodiment 3.

FIG. 12 shows a first procedure of processing by the service providing system 3 of the present embodiment. Any step where the same process as in FIG. 8 is performed is denoted by the same numeral and the description thereof is omitted. First, step S101 to step S111 are identical to the processing of FIG. 8.

At step S301, the determination section 600 notifies the determination result to the option-for-presentation selection section 601 if the determination result indicates having "thought to be the correct answer". Upon receiving the notice, the option-for-presentation selection section 601 outputs a correct answer which is described in the question DB 203 via the output section 101, and stops presenting any subsequent answer options.

Through such processing, when it is determined that the user has thought a given answer option to be the correct answer, no subsequent answer options are presented; thus, presentation of unnecessary answer options can be reduced, whereby a more efficient study assistance is realized.

Figure 13:
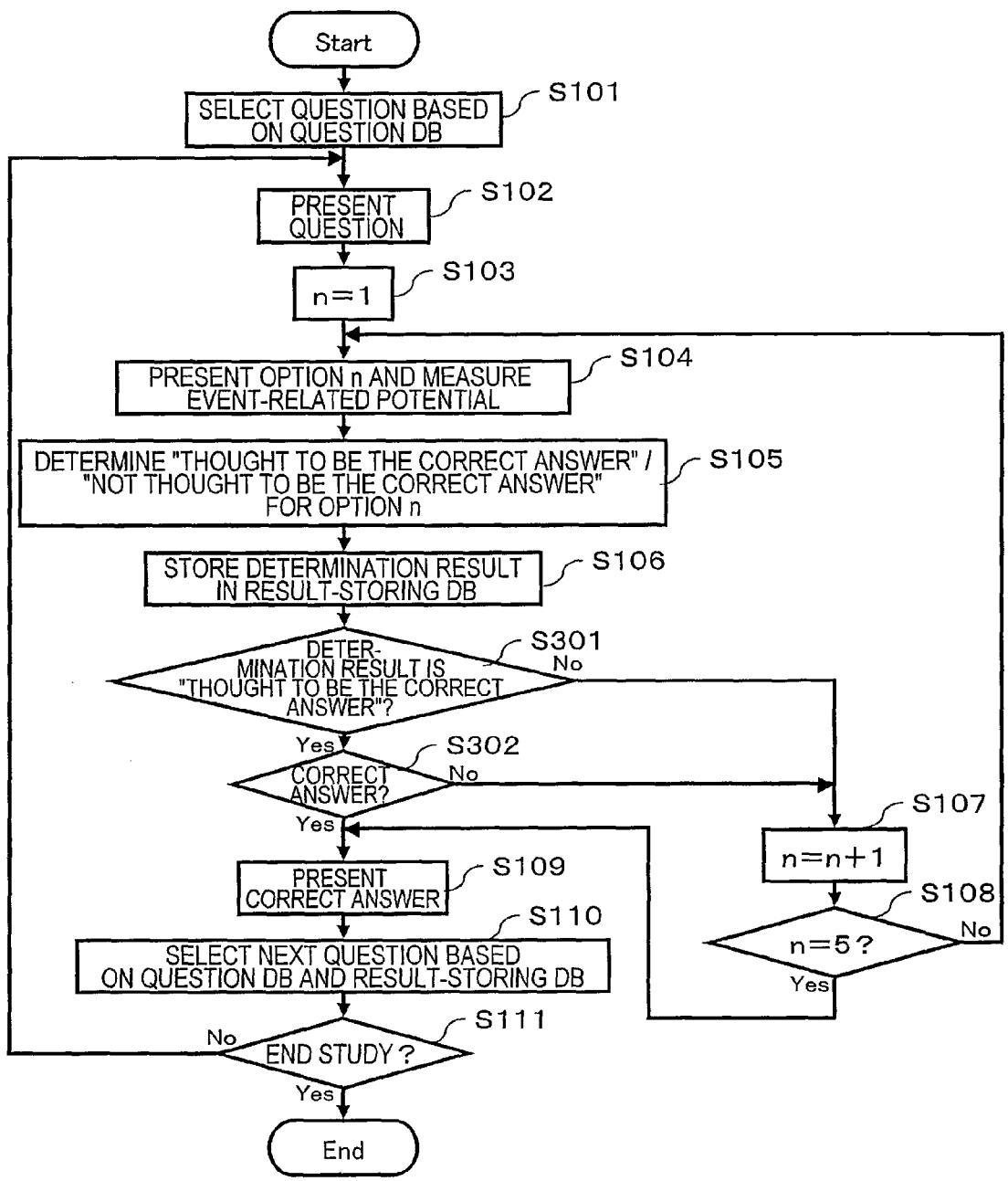
FIG. 13 A flowchart showing a second procedure of processing by the service providing system 3 according to Embodiment 3.

The processing shown in FIG. 12 can be further modified to the processing shown in FIG. 13. FIG. 13 shows a second procedure of processing by the service providing system 3 according to the present embodiment. The processing shown in FIG. 13 compares an answer option which has been determined by the determination section 600 as being "thought to be the correct answer" and an actually correct answer option described in the question DB 203, and presents a next answer option when it is incorrect.

In FIG. 13, any step where the same process as in FIG. 12 is performed is denoted by the same numeral and the description thereof is omitted. First, step S101 to step S111 and step S301 are identical to the processing of FIG. 12.

At step S302, the option-for-presentation selection section 601 compares the option which has been determined by the determination section 600 as being "thought to be the correct answer" and the actually correct answer option described in the question DB 203, and if they match, stops presenting any subsequent answer options, and the process proceeds to S109. If they do not match, the process proceeds to step S107 and after, and the option-for-presentation selection section 601 presents a next answer option.

Through such processing, subsequent answer options are prevented from being presented only if an option which has been determined as being thought to be the correct answer by the user is the correct answer. As a result, presentation of unnecessary answer options can be reduced, and a more efficient study assistance is realized.

Figure 14:
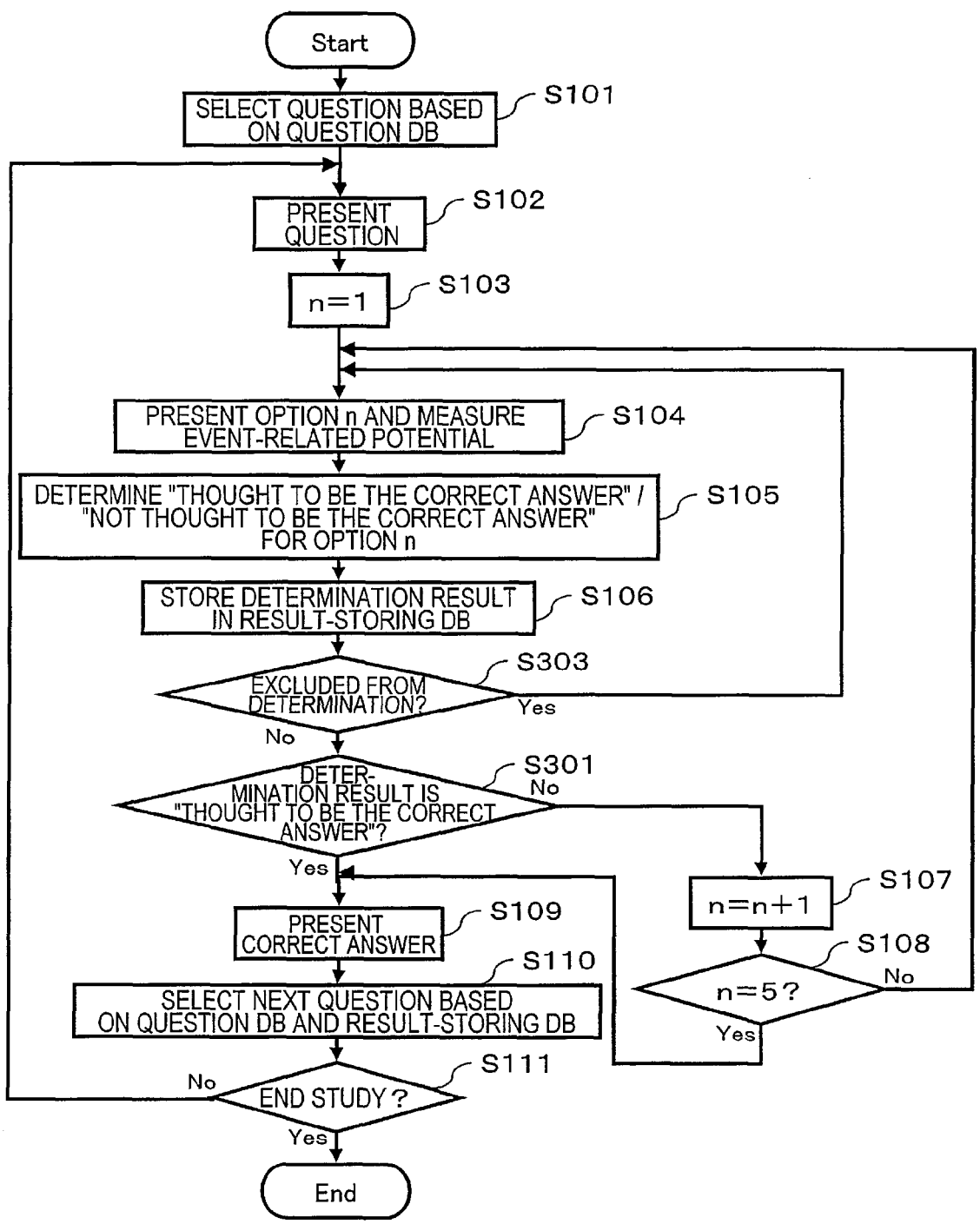
FIG. 14 A flowchart showing a third procedure of processing by the service providing system 3 according to Embodiment 3.

Furthermore, the processing shown in FIG. 13 can be modified to the processing shown in FIG. 14. FIG. 14 shows a third procedure of processing by the service providing system 3 of the present embodiment. In the processing shown in FIG. 14, any option in which noises (e.g. electroocular) were mixed and which were excluded from determination by the determination section 600 is again presented, and again subjected to determination.

In FIG. 14, any step where the same process as in FIG. 12 is performed is denoted by the same numeral and the description thereof is omitted. The difference is that, in the processing shown in FIG. 14, step S303 is provided between step S106 and step S301 of FIG. 12.

At step S303, upon receiving a notice that the event-related potential of the user 50 which has been measured by using the point of option presentation as a starting point has been excluded from determination by the determination section 600 because noises (e.g. electroocular) are mixed therein, the option-for-presentation selection section 601 again presents that answer option.

Through such processing, it becomes possible to again present any option which has been excluded from determination because noises (e.g. electroocular) were mixed in the event-related potential measured by using the point of option presentation as a starting point. Thus, options which cannot be determined are reduced, and an option which has been thought by the user to be the correct answer can be identified with a higher precision.

Note that, when the option-for-presentation selection section 601 selects an option for presentation by referring to the question DB 203, an option which is the correct answer may be presented at an early stage. For example, assuming that the number of options is n, the option which is the correct answer may be presented at the $(n/2)^{th}$ or earlier. Alternatively, an option which is the correct answer may be presented at the $(n/3)^{th}$ or even earlier. As a result, presentation of options can be reduced.

In accordance with the service providing system 3 of the present embodiment, the service providing system 3 is constructed by using the service providing apparatus 12. As a result, it becomes possible to switch between methods of presenting answer options in accordance with the determination result of the user state. That is, presentation of unnecessary options can be reduced and necessary options can be again presented, whereby a more efficient study assistance without answer inputs can be realized.

3-4. EMBODIMENT 4

3-4-1. Detailed Construction of a Service Providing System According to Embodiment 4

Next, a service providing system and service providing apparatus according to Embodiment 4 of the present invention will be described.

The service providing system according to Embodiment 1 was embodied as a study system, based on the experimental results which were described in the beginning. In a study system, an option which the user has thought to be the correct answer is determined by using the event-related potential of a user, and a study assistance in a manner similar to when there is an answer input is realized.

However, the above experimental results are also applicable to systems other than study systems. By utilizing the aforementioned experimental results, it becomes possible to determine an appliance operation that is desired by a user. Therefore, an information appliance can be realized which, without a manipulation input, executes an appliance operation that is desired by a user. For example, when the user uses a portable terminal on a train or the like, the portable terminal being capable of recording and playing back TV programs, the user is able to select from among the recorded programs a program that he or she desires to watch at that point in time, without a manipulation input.

In the present embodiment, instead of presenting a study question in the experiment described in the beginning, a question concerning an appliance operation which the user wants to realize by using the information appliance (e.g. "Which recorded program do you want to watch?") is presented. Then, instead of answer options for the question, prospective services (e.g. program names of recorded programs) which the appliance can provide are consecutively presented.

When the user has imagined the program name of a program to be played back in advance and a plurality of program names are being consecutively presented, the user is waiting for the imagined program name to be presented. The psychological state at this time is considered to be the same as the psychological state where the user is waiting for the presentation of an answer option which he or she has thought to be the correct answer in the above Embodiments. Then, if the appliance operation name imagined by the user matches the appliance operation name which is described in the option that is presented by the service providing apparatus 13, it means to the user that an option which is the "correct answer" has been presented by the appliance. That is, it can be said that the user has thought that option to be the "correct answer". Therefore, by using a portion of the event-related potential at about 400 milliseconds since the timing at which the option is output via the output section 101 as a starting point, it becomes possible to automatically detect whether the appliance operation name imagined by the user matches the appliance operation name described in the option presented by the service providing apparatus 13 or not.

As a result, there is realized a service providing system which realizes a desired appliance operation without any manipulation inputs, in a situation where it is difficult to make a manipulation input, e.g., within a train, or in a situation where the user is unable to perform a manipulation input operation or does not perform a manipulation input operation.

Hereinafter, a service providing system which realizes a desired appliance operation without a manipulation input will be described.

Figure 15:
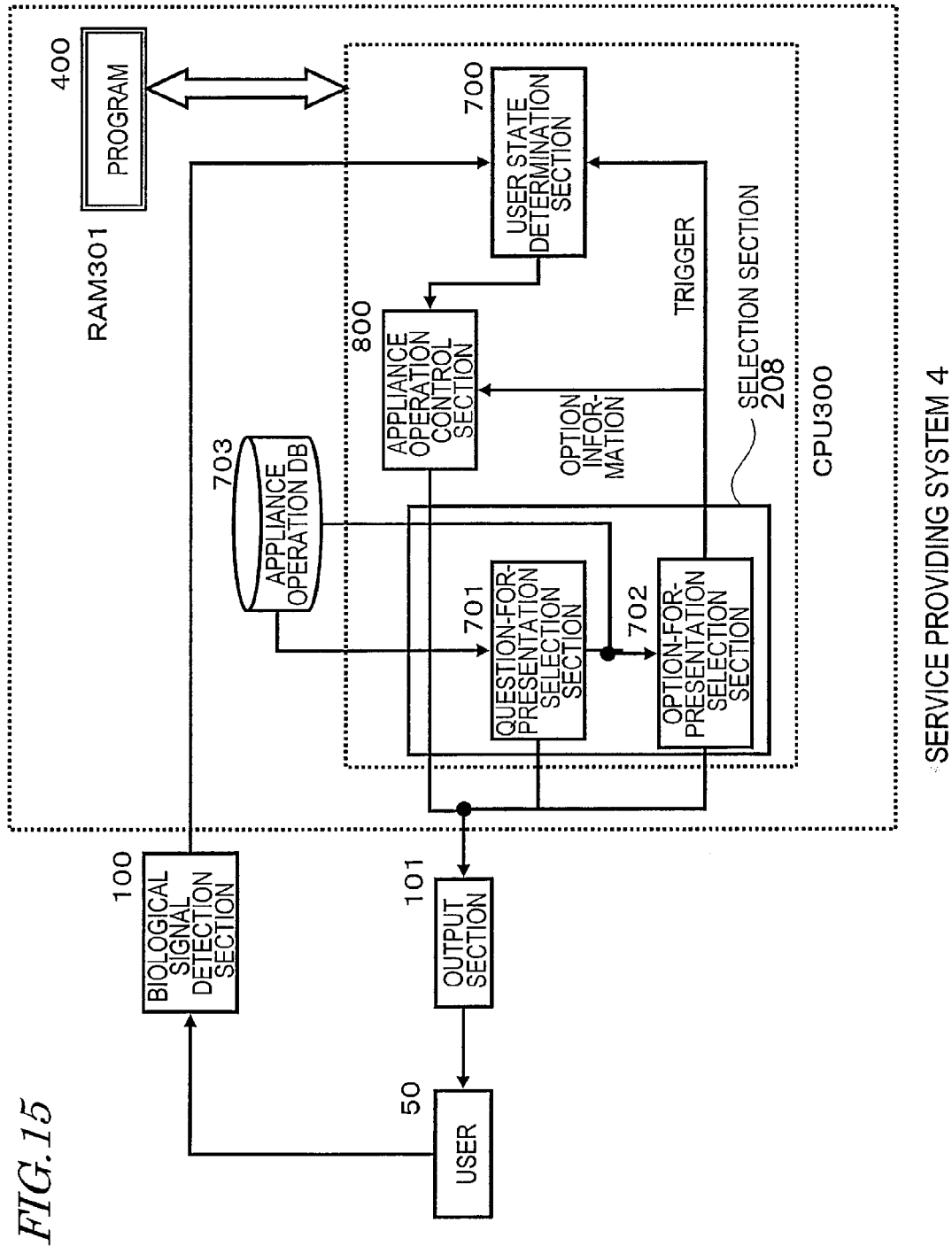
FIG. 15 A diagram showing the functional block construction of a service providing system 4 according to Embodiment 4.

FIG. 15 shows the functional block construction of the service providing system 4 according to the present embodiment. FIG. 15 also shows detailed functional blocks of the service providing apparatus 13. Note that the user 50 block is shown for convenience of description. The service providing apparatus 13 shown in FIG. 15 is an information appliance such as a PDA or mobile phone.

In FIG. 15, any component element which is the same as that in FIG. 2 is denoted by the same numeral and the description thereof is omitted. From the service providing apparatus 10 shown in FIG. 2, the service providing apparatus 13 shown in FIG. 15 differs in that the following are comprised: a question-for-presentation selection section 701 for presenting operations (functions) that are providable by the service providing apparatus 13 (information appliance) in the form of questions; an option-for-presentation selection section 702 for selecting a prospective appliance operation; an appliance operation DB 703 for storing a list of questions and prospective appliance operations concerning the functions of the information appliance; and a user state determination section (hereinafter "determination section") 700 for determining whether it is an option that the user wanted to select are comprised. Note that, as in the Embodiments above, the question-for-presentation selection section 701 and the option-for-presentation selection section 702 are included in the selection section 208, and the selection section 208 is realized by the operation of the CPU 300.

In the following description, it is assumed that the service providing apparatus 13 is a portable terminal on which TV programs can be recorded and played back.

The question-for-presentation selection section 701 refers to the appliance operation DB 703 described later, and presents a function which the user can realize on the information terminal, in the form of a question. For example, "Which recorded program do you want to play back?" or "Which recorded program do you want to erase?". In the case where it is possible to play back music or play games on this portable terminal, it may be "Which function (playback program/playback music/game) do you want to use?", for example. The order of questions to be presented may be determined according to the order in which they are stored in the appliance operation DB 702, or determined in accordance with the situation of the user or the surrounding situation.

The option-for-presentation selection section 702 refers to the appliance operation DB 703, and selects an option of a prospective appliance operation which is in accordance with the question selected by the question-for-presentation selection section 701. At the question-for-presentation selection section 701, if "Which recorded program do you want to watch?" is selected, a recorded program name is selected. The selected program name is output in a character sequence via the output section 101.

The appliance operation DB 703 stores questions concerning functions that can be realized on the terminal and prospective appliance operations as options. FIG. 16 shows specific examples of data concerning the questions stored in the appliance manipulation DB 703. In accordance with the number of appliance operations that can be realized, the appliance operation DB 703 retains a plurality of options. Note that the options need to be plural, although the number thereof is not limited. Moreover, data concerning the orders of presenting questions may be stored in addition to the questions and options.

Note that the latest situation must always be reflected by the appliance operation DB 703. For example, if a program is recorded, that program name is added, and if a recorded program is erased, that program name is erased. Such updates may be made based on instructions from a circuit which controls recording, playback, and the like of programs, or may be performed by the CPU 300.

By a method similar to that of the determination section 200 described above, based on a biological signal from the user 50 as detected by the biological signal detection section 100, the determination section 700 detects an option which the user wanted to select, and notifies it to an appliance operation control section 800.

The appliance operation control section 800 receives an option concerning the appliance operation which has been selected by the option-for-presentation selection section 702, and if it is an option which the user wanted to select according to the determination section 700, executes the target appliance operation. For example, if the option selected by the option-for-presentation selection section 702 is program C, program C is played back.

3-4-2. Processing by the Service Providing System According to Embodiment 4

Next, with reference to the flowchart of FIG. 17, an overall flow of processes to be performed by the service providing system 4 of FIG. 17 will be described.

Figure 17:
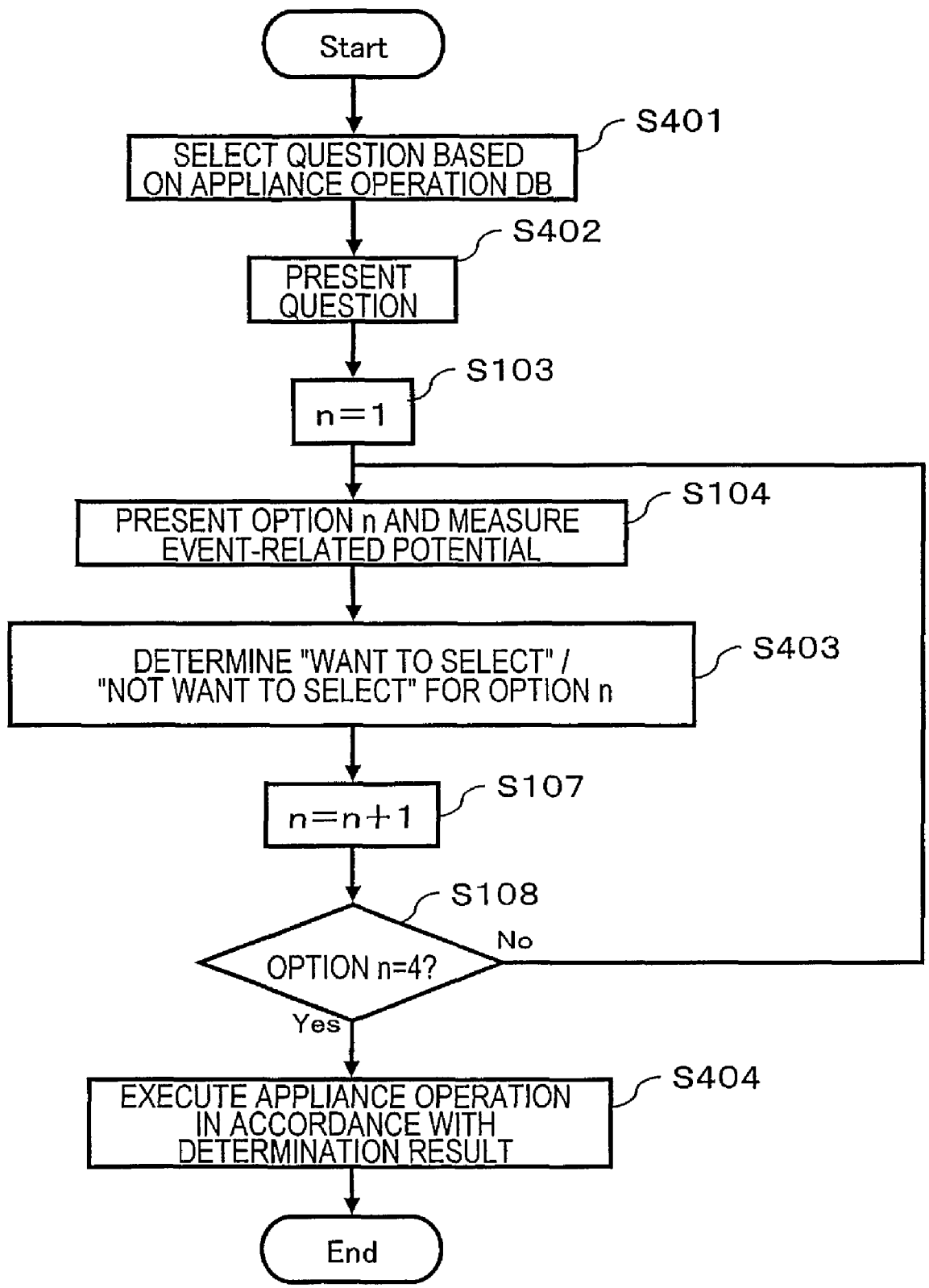
FIG. 17 A flowchart showing a procedure of processing by the service providing system 4 according to Embodiment 4.

FIG. 17 shows a procedure of processes by service providing system 4 of the present embodiment. Any step where the same process as in FIG. 8 is performed is denoted by the same numeral and the description thereof is omitted.

At step S401, the question-for-presentation selection section 701 selects a question to be presented to the user 50 by referring to the appliance operation DB 703.

At step S402, the question selected at step S401 is output to the user 50 via the output section 101.

At step S403, from the waveform of the event-related potential at about 400 milliseconds since a starting point which is the trigger received at step S104, the determination section 700 determines whether the user wanted to select the presented option or not.

At step S404, based on the result determined by the determination section 700 at step S403 and the option information acquired from the option-for-presentation selection section 702, the appliance operation control section 800 executes the option which the user wanted to select. Through such processing, the option which the user wanted to select can be determined.

By constructing the service providing system 4 with the service providing apparatus 13, it becomes possible to determine whether it is an option that a user wanted to select, using an event-related potential since presentation of a prospective appliance operation as a starting point. Therefore, an information appliance can be realized which, without a manipulation input such as pressing of a button, executes an appliance operation that the user desires.

INDUSTRIAL APPLICABILITY

The service providing apparatus and the service providing system according to the present invention are able to determine which option a user has thought to be the correct answer while merely looking at a question and answer options that are consecutively presented, without an answer input. As a result, even during study without answer inputs, a study system which can provide study assistance in a manner similar to when there is an answer input is realized, in situations where it is difficult to make an answer input, e.g., a train, and in situations where no answer input is made.

The invention claimed is:

1. A service providing system comprising:
    an output section for presenting a question to a user, and further presenting sequentially a plurality of options as candidate answers to the question;
    a signal detection section for measuring an event-related potential of electroencephalograms of the user for each of the plurality of options in a predetermined period after each option is presented;
    a determination section for determining an option from among the plurality of options that the user has thought to be a correct answer, based on the event-related potentials in the predetermined period after each option is presented;
    a database storing a plurality of questions as well as options which are correct answers to the plurality of questions and options which are not the correct answers; and
    a selection section for, when the option which is determined by the determination section to have been thought to be the correct answer by the user corresponds to an option described as a correct answer option in the database, selecting a question of a genre different from that of the question presented by the output section,
    wherein the output section presents an option which is the correct answer in a first half of the presented plurality of options.

2. The service providing system of claim 1, wherein the determination section determines whether the user has thought each option to be a correct answer or not, by using as the predetermined period a period from about 350 milliseconds to about 450 milliseconds as counted from a point in time where each option is presented.

3. The service providing system of claim 1, further comprising a selection section for selecting the question by referring to the database, and thereafter selecting the option which is the correct answer and the option which is not the correct answer in an arbitrary order and sending the option to the output section, wherein,
    when beginning boot of the service providing system or when receiving an instruction from the user,
    based on an event-related potential after presenting the option which is the correct answer and an event-related potential after presenting the option which is not the correct answer, the determination section executes a calibration for the event-related potential related to the user having thought it to be the correct answer.

4. The service providing system of claim 1, further comprising a timing control section for determining whether the user is in a stand-by state or not based on the event-related potential in a predetermined period before presenting each option, and giving an instruction to select and output a next option in accordance with a determination result.

5. The service providing system of claim 1, wherein, when the determination section determines that the user has thought the presented option to be the correct answer, the output section does not present any option that is left as a candidate answer to the question.

6. The service providing system of claim 1, wherein, when determining that the user has thought the presented option to be the correct answer, the determination section further determines whether the presented option matches the option which is the correct answer or not; and if they match, the output section does not present any option that is left as a candidate answer to the question.

7. The service providing system of claim 6, wherein, when determining that the user has thought the presented option to be the correct answer, the determination section presents the option which is the correct answer.

8. The service providing system of claim 1, wherein, when detecting that noise is mixed in the event-related potential based on the event-related potential, the determination section quits the determination as to whether the user has thought the presented option to be the correct answer; and the output section again presents the option.

9. The service providing system of claim 1, wherein, the determination section previously retains, regarding a predetermined question, a threshold which lies between an average potential of an event-related potential in a time slot from 300 milliseconds to 500 milliseconds after presenting an option which is determined as having been thought to be the correct answer by the user and an average potential of an event-related potential in the time slot, which is determined as having not thought to be the correct answer; and the determination section compares between the threshold and the average potential of the event-related potential in the time slot, and determines that the user has thought it to be the correct answer if the average potential is greater than the threshold, and determines that the user has not thought it to be the correct answer if the average potential is smaller than the threshold.

10. The service providing system of claim 1, wherein, the determination section retains, regarding a predetermined question, first numerical values which are pre-generated based on an average potential of an event-related potential in a time slot from 300 milliseconds to 500 milliseconds after presenting an option which is determined as having been thought to be the correct answer by the user and second numerical values which are pre-generated based on an average potential of an event-related potential in the time slot, which is determined as having not thought to be the correct answer; and the determination section compares a first Mahalanobis distance between the average potential of the event-related potential in the time slot and the first numerical values against a second Mahalanobis distance between the average potential and the second numerical values, and determines that the user has thought it to be the correct answer if the first Mahalanobis distance is shorter than the second Mahalanobis distance, and determines that the user has not thought it to be the correct answer if the first Mahalanobis distance is longer than the second Mahalanobis distance.

11. The service providing system of claim 1, wherein the determination section retains, regarding a predetermined question, a first template which is pre-generated based on an event-related potential in a time slot from 300 milliseconds to 500 milliseconds after presenting an option which is determined as having been thought to be the correct answer by the user and a second template which is pre-generated based on an event-related potential in the time slot, which is determined as having not thought to be the correct answer; and the determination section compares a first correlation coefficient between a waveform value of the event-related potential in the time slot and the first template against a second correlation coefficient between the waveform value and the second template, and determines that the user has thought it to be the correct answer if the first correlation coefficient is greater than the second correlation coefficient, and determines that the user has not thought it to be the correct answer if the first correlation coefficient is smaller than the second correlation coefficient.

12. The service providing system of claim 1, wherein the determination section retains an average value of the event-related potential corresponding to each of the plurality of options, and determines that an option having a largest average value has been thought to be the correct answer by the user.

13. The service providing system of claim 10, wherein, among the event-related potentials corresponding respectively to the plurality of options, the determination section determines that an option having a shortest Mahalanobis distance from the first numerical values has been thought to be the correct answer by the user.

14. The service providing system of claim 11, wherein, among the event-related potentials corresponding respectively to the plurality of options, the determination section determines that an option having a largest first correlation coefficient has been thought to be the correct answer by the user.

15. A quizzing method comprising:

a presentation step of presenting a question to a user;

a sequential presentation step of sequentially presenting a plurality of options as candidate answers to the question;

a measurement step of measuring an event-related potential of electroencephalograms of the user for each of the plurality of options in a predetermined period after each option is presented;

a determination step of determining an option from among the plurality of options that the user has thought to be a correct answer, based on the event-related potentials in the predetermined period after each option is presented;

a storing step of storing in a database a plurality of questions as well as options which are correct answers to the plurality of questions and options which are not the correct answers; and a selection step of, when the option which is determined by the determination step to have been thought to be the correct answer by the user corresponds to an option described as a correct answer option in the database, selecting a question of a genre different from that of the question presented by the presentation step, wherein the sequential presentation step comprises presenting an option which is the correct answer in a first half of the presented plurality of options.

16. The service providing system of claim 1, wherein, when an option determined by the determination section to have been thought to be the correct answer by the user is described as an option which is not a correct answer in the database, the selection section selects a question of a same genre as the question presented by the output section.

17. The service providing system of claim 1, wherein when there is no option determined by the determination section to have been thought to be the correct answer by the user, the selection section selects the same question as the question presented by the output section.

18. The service providing system of claim 1, wherein the output section presents the question selected by the selection section.

* * * * *